(12) United States Patent
Belt

(10) Patent No.: US 12,270,006 B2
(45) Date of Patent: Apr. 8, 2025

(54) COATING COMPOSITION, METHOD OF MAKING A HYDROPHILIC COATING ON A SUBSTRATE, AND MEDICAL DEVICE COMPRISING SUCH COATING

(71) Applicant: DSM IP Assets B.V., Heerlen (NL)

(72) Inventor: Johannes Wilhelmus Belt, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 118 days.

(21) Appl. No.: 17/925,425

(22) PCT Filed: May 11, 2021

(86) PCT No.: PCT/EP2021/062541
§ 371 (c)(1),
(2) Date: Nov. 15, 2022

(87) PCT Pub. No.: WO2021/233743
PCT Pub. Date: Nov. 25, 2021

(65) Prior Publication Data
US 2023/0183596 A1   Jun. 15, 2023

(30) Foreign Application Priority Data

May 18, 2020 (EP) .................................... 20175279

(51) Int. Cl.
*C10M 169/04* (2006.01)
*A61L 29/08* (2006.01)
(Continued)

(52) U.S. Cl.
CPC ....... *C10M 169/044* (2013.01); *A61L 29/085* (2013.01); *C10M 107/42* (2013.01); *C10M 107/44* (2013.01); *C10M 129/24* (2013.01); *C10M 145/38* (2013.01); *C10M 161/00* (2013.01); *C10M 177/00* (2013.01); *A61L 2400/10* (2013.01); *A61L 2420/02* (2013.01); *A61L 2420/06* (2013.01); *C10M 2207/08* (2013.01); *C10M 2209/109* (2013.01); *C10M 2217/0285* (2013.01);
(Continued)

(58) Field of Classification Search
CPC ............ C10M 169/044; C10M 107/42; C10M 107/44; C10M 129/24; C10M 145/38; C10M 161/00; C10M 177/00; C10M 2207/08; C10M 2209/109; C10M 2217/0285; C10M 2217/0453; C10M 2217/065; A61L 29/085; A61L 2400/10; A61L 2420/02; A61L 2420/06; A61L 29/145; C10N 2040/50; C10N 2050/023; C10N 2070/00; C08F 2/48; C08F 222/1063; C08F 222/1065; C08F 271/02; C08F 222/102; C08F 222/385; C08F 2/50; C08G 18/4825; C08G 18/4854; C08G 18/672; C08G 18/755; C08G 18/7621; C08G 18/48; C09D 175/16; C09D 4/06; C08L 75/04
See application file for complete search history.

(56) References Cited

U.S. PATENT DOCUMENTS

| | | |
|---|---|---|
| 2010/0076546 A1 | 3/2010 | Dias et al. |
| 2018/0312697 A1 | 11/2018 | Gotou et al. |

FOREIGN PATENT DOCUMENTS

| | | |
|---|---|---|
| CN | 108137981 | 6/2018 |
| EP | 0591091 A1 | 4/1994 |

(Continued)

OTHER PUBLICATIONS

International Search Report and Written Opinion dated Jul. 21, 2021.

(Continued)

*Primary Examiner* — Taiwo Oladapo
(74) *Attorney, Agent, or Firm* — NIXON & VANDERHYE P.C.

(57) ABSTRACT

The disclosure relates to a coating composition comprising a polymerizable compound of formula [1], wherein G is a residue of a hydrophobic hydroxy-functional oligomer, n is 1-10, each R1 independently is a residue of a $C_6$-$C_{20}$ aliphatic, cycloaliphatic, or aromatic hydrocarbon compound, and Z is a moiety having a polymerizable group; Formula [1] a hydrophilic polymer; a photo-initiator; optionally one or more further components, and a solvent. The polymerizable compound of formula [1] is typically present in an amount of 2.0-30 mass % based on total dry mass of the composition. Such coating composition can be made into a well-adhering single-layer hydrophilic coating on a surface of polymer substrates without providing a primer layer or chemically modifying the surface of the substrate. Upon wetting, the coating shows excellent lubricity and durability. In further aspects, the disclosure provides a method of applying a hydrophilic and optionally lubricious coating to an article; and an article like a medical device having on at least part of its surface a single-layer, hydrophilic and optionally lubricious coating, like a catheter, guidewire, or a delivery device for an implant.

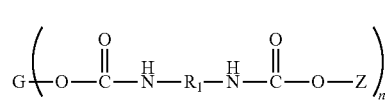

[1]

18 Claims, No Drawings

(51) Int. Cl.
*C10M 107/42* (2006.01)
*C10M 107/44* (2006.01)
*C10M 129/24* (2006.01)
*C10M 145/38* (2006.01)
*C10M 161/00* (2006.01)
*C10M 177/00* (2006.01)
C10N 40/00 (2006.01)
C10N 50/00 (2006.01)
C10N 70/00 (2006.01)

(52) U.S. Cl.
CPC ............... *C10M 2217/0453* (2013.01); *C10M 2217/065* (2013.01); *C10N 2040/50* (2020.05); *C10N 2050/023* (2020.05); *C10N 2070/00* (2013.01)

(56) References Cited

FOREIGN PATENT DOCUMENTS

| | | |
|---|---|---|
| EP | 2173397 A2 | 4/2010 |
| WO | 2006056482 A1 | 6/2006 |
| WO | 2007065720 A2 | 6/2007 |
| WO | WO-2008031596 A1 * | 3/2008 ........... A61L 29/085 |

OTHER PUBLICATIONS

The First Office Action, CN Application No. 202180035396.1, Dec. 30, 2024.

* cited by examiner

COATING COMPOSITION, METHOD OF MAKING A HYDROPHILIC COATING ON A SUBSTRATE, AND MEDICAL DEVICE COMPRISING SUCH COATING

CROSS-REFERENCE TO RELATED APPLICATIONS

This application is a U.S. national phase entry under 35 USC § 371 of International Application No. PCT/EP2021/062541, filed 11 May 2021, which itself claims priority to European Application No. EP20175279.7, filed 18 May 2020, the entire contents of each of which is hereby incorporated by reference in its entirety as if fully set forth herein.

FIELD

The disclosed inventions relate to a photo-curable coating composition for making a hydrophilic coating on a substrate, which coating becomes lubricious upon wetting with a wetting agent. The inventions also relate to methods of making a hydrophilic coating or a lubricious coating on a substrate, like on a surface of a medical device or a component thereof; and to such coated component or medical device, like a catheter for endovascular or urological applications.

BACKGROUND

Medical devices such as intravascular devices like guide wires, introducers, catheters and intermittent catheters, are to be inserted into and subsequently removed from a tortuous pathway in the body to perform their function without causing a patient discomfort or irritating or damaging a patient's soft tissue. For this reason the surface of such devices need to be lubricious or slippery. Lubricious surface properties may not only ease maneuvering within a patient's vasculature and minimize soft tissue damage, but also facilitate drainage of fluids from the body. Therefore, such medical devices often contain a hydrophilic surface layer or coating, which coating becomes lubricious and attains low-friction properties upon wetting and absorbing water, for example by applying an aqueous wetting fluid for a certain time period prior to insertion of the device into the body of a patient or upon insertion by contacting a body liquid.

Relevant properties of such (lubricious) hydrophilic coating for use on a medical device include, in addition to biocompatibility and low friction properties in wetted state, a low amount of extractables, good adhesion to the surface, and high durability or abrasion resistance to prevent release of particulate material during use.

Most hydrophilic coatings are based on a crosslinked water-soluble polymer, which has a relatively low crosslink density and will readily uptake water when exposed to a source, and will swell, sometimes even to several times the thickness in the dry state, to form a hydrogel-like layer. Many medical devices like guide wires and catheters are made from metals or flexible plastic materials like polyolefins, PVC, polyamide 12, or polyamide blockcopolymers and polyurethanes. Generally, adhesion of a hydrophilic polymer to such substrate surface is insufficient to meet requirements for use as coating on a medical device. Therefore, depending on the substrate a pretreatment may be needed, like a chemical modification of the surface using for example a plasma or corona treatment, and/or applying a primer or base coat layer in order to enhance the level of adhesion between substrate and hydrophilic coating.

In WO2007/065720A2 a 2-layered hydrophilic coating for a urinary catheter is described, which comprises a primer layer and a topcoat layer, made by applying and UV-curing a non-aqueous primer composition comprising a polyether having polymerizable groups and a photo-initiator, and subsequently an aqueous topcoat composition comprising non-ionic and ionic hydrophilic polymers and a photo-initiator, respectively.

A photo-curable hydrophilic coating composition comprising an acrylamide-functional polymerizable compound, a non-ionic hydrophilic polymer and optionally an ionic hydrophilic polymer, and a photo-initiator is disclosed in WO2008/031596A1, which composition is used to form a 2-layer hydrophilic coating on a polymeric surface of a medical device, applying a primer layer with a composition as for example in as described in WO2006/056482A1 or in WO2007/065720A2.

EP0591091A1 proposes a coating composition that would result in a durable, single-layer lubricious coating on a substrate, which composition is an aqueous solution of a hydrophilic polymer and optionally an osmolality-increasing compound, wherein a polymerizable binder compound that is not soluble in water is present in dispersed state to improve adhesion.

A hydrophilic coating solution as described in EP2173397A2 comprises in addition to a multifunctional acrylic network-forming component, a hydrophilic polymer and two photoinitiators, also an acid-functionalized acrylate as adhesion promoter. This last compound would co-react with the network-forming component and bind to the polymer surface of a substrate like a catheter.

Disadvantages of known coating compositions and systems may include limited shelf-life of compositions; 2-layer systems and/or long curing times resulting in relatively high production costs. Also, cured coatings may show too high level of leachables or extractables, and insufficient mechanical robustness; especially after being wetted and swollen with water. Although various improvements have been proposed or described in literature, there still appears a need for a coating composition that can be efficiently processed and applied as a hydrophilic coating on various substrates, preferably showing such level of adhesion that use of a chemical surface pretreatment or of a primer coating may be omitted, and which cured coating becomes lubricious upon contacting with a wetting agent and shows balanced combination of adhesion and durability.

SUMMARY

It is an object of present disclosure to provide a coating composition that overcomes at least part of said problems, that is a coating composition stable in storage, efficiently applicable as a single-layer hydrophilic coating on a substrate, and/or resulting in a coating showing robust lubricity when wetted.

The aspects and embodiments as described herein below and as characterized in the claims provide a photo-curable coating composition, which is suitable for making a hydrophilic coating on a substrate and which coating becomes lubricious upon contacting with a wetting agent, and which composition can be efficiently applied and cured to form a single-layer hydrophilic coating on various substrates while showing good adhesion, lubricity and durability in use. An aspect of the invention is thus a coating composition according to the claims, more specifically a photo-curable coating composition suitable for making a hydrophilic coating that becomes lubricious upon wetting, which composition comprises (a) A polymerizable compound of formula [1], wherein G is a residue of a hydrophobic hydroxy-functional oligomer; n is 1-10, each $R_1$ independently is a residue of a $C_6$-$C_{20}$ aliphatic, cycloaliphatic, or aromatic hydrocarbon compound, and Z is a moiety having a polymerizable group;

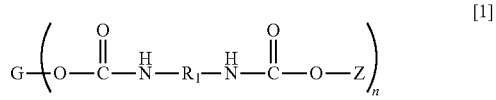

[1]

(b) A hydrophilic polymer;
(c) A photo-initiator;
(d) Optionally one or more further components,
(e) A solvent for components (a)-(c); and wherein the polymerizable compound of formula [1] is present in an amount of 2.0-30 mass % based on total dry mass of the composition.

It was surprisingly found that such coating composition can be made into a well-adhering single-layer hydrophilic coating on a surface of various polymer substrates like aliphatic polyamides, polyamide block copolymers, polyurethanes and polyvinylchloride, typically without needing to provide an adhesion-promoting primer layer or to chemically modify the surface of the substrate. The coating composition is stable, allowing storage for several years before use, and can be efficiently applied to a substrate using conventional coating equipment with relatively short cycle times. Upon wetting, e.g. with an aqueous wetting agent, the coating shows excellent lubricity and durability.

It may be that EP0591091A1 also discloses a coating composition for making a single-layer hydrophilic coating on a substrate, but herein it is taught that only if a hydrophobic polymerizable binder compound is dispersed, and not dissolved, in an aqueous solution of the other components it is possible to obtain a coating with sufficient adhesion. A disadvantage of such composition may be limited stability and shelf life.

In US2018/0312697A1 radiation-curable coating compositions are described, which contain an acrylic polymer having polymerizable groups, a compound having multiple polymerizable groups, a urethane (meth)acrylate having 2-4 polymerizable groups, and a photoinitiator. A cured, highly crosslinked coating layer can be made therefrom, which has excellent appearance and shows repairability from surface damage like scratches. Such coatings lack the ability to absorb significant amounts of water, which would be needed to become a hydrogel showing lubricity. The urethane (meth)acrylate compounds applied do not contain the residue of a hydrophobic hydroxy-functional oligomer.

In another aspect, the invention relates to a hydrophilic coating that is obtained by curing a layer of the coating composition according to the invention.

A further aspect of the invention concerns a method of applying a hydrophilic and optionally lubricious coating to an article comprising steps of Applying a coating composition according to the invention to at least a part of a surface of the article;
At least partly removing the solvent from the applied coating composition;

Curing the applied coating composition by exposing to UV-light during or after removing solvent to form a hydrophilic coating; and
optionally contacting the hydrophilic coating with a wetting fluid to form a lubricious coating.

Another aspect of the invention relates to an article like a medical device having on at least part of its surface a single-layer hydrophilic and optionally lubricious coating, which article is obtained by the method of the invention. Examples of articles that can benefit from having such coating include endovascular devices like cardiovascular and neurovascular devices; urological devices for treatment of the urinary tract or urogenital system; and devices for use in ophthalmology; such as for example catheters, guidewires, and delivery devices for e.g. heart valve prostheses or intraocular lenses.

Although the description is generally related to and illustrated with polyether diol-based polymerizable compounds, also other hydrophobic, oligomeric or polymeric compounds having endgroups that can react with an isocyanate group can be used to make polymerizable compounds suitable for use in the coating compositions.

DETAILED DESCRIPTION OF EMBODIMENTS

A coating or surface layer that can become lubricious or slippery upon contacting with a wetting agent like an aqueous composition is herein referred to as a hydrophilic coating; such coating obtained after wetting, which is typically a hydrogel, is referred to as a lubricious coating.

Within the context of present disclosures, hydrophobicity refers to the physical property of a molecule or surface that is seemingly repelled by water, in contrast to hydrophilicity that refers to attracting water. Hydrophobic compounds tend to be nonpolar, and prefer other neutral molecules and nonpolar solvents. Water molecules being polar, most hydrophobic compounds have limited water solubility or are insoluble in water. Depending on their structure, hydrophobic molecules may cluster together in water, forming droplets or in presence of surfactants micelles or other semi-ordered structures.

A single-layer coating refers to a coating layer that has been applied on a substrate from one coating composition, in one or optionally more coating steps; in contrast to for example a two-layer coating that has been applied from two different coating compositions, like a primer and a top coat composition. With a primer is meant a coating composition or an undercoat, which is applied to a substrate surface to enhance adhesion of a subsequent top coat, which provides certain functionality, but shows insufficient adhesion when directly applied to the substrate surface.

In accordance with an aspect, the invention provides a photo-curable coating composition, which is suitable for making a hydrophilic coating, which composition comprises (a) A polymerizable compound of formula [1], wherein G is a residue of a hydrophobic hydroxy-functional oligomer; n is 1-10, each $R_1$ independently is a residue of a $C_6$-$C_{20}$ aliphatic, cycloaliphatic, or aromatic hydrocarbon compound, and Z is a moiety having a polymerizable group;

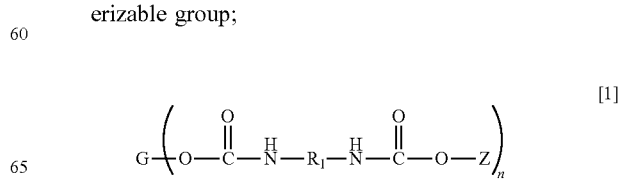

[1]

(b) A hydrophilic polymer;
(c) A photo-initiator;
(d) Optionally one or more further components, and
(e) A solvent for components (a)-(c);
wherein the polymerizable compound of formula [1] is present in an amount of 2.0-30 mass % based on total dry mass of the composition.

The present coating composition is photo-curable, which means that the composition can be reacted or cross-linked to form a non-soluble, but water-swellable hydrophilic polymer network by exposing to electromagnetic radiation. The intensity and wavelength of said radiation can be chosen, dependent on the type and amount of photo-initiator and polymerizable or reactive components present and on the desired cross-link density. In particular, a suitable wavelength in the UV, visible or IR part of the spectrum may be used; typically a UV light source is used to initiate curing. E-beam and high energy radiation like gamma may also be applied for curing of the coating. The skilled person will be able to select a suitable radiation source and conditions, based on his knowledge, present disclosure, and optionally some experiments.

Polymerizable Compound of Formula [1]

The coating composition for making a hydrophilic coating comprises at least one polymerizable compound of formula [1]; also referred to as component (a). The composition may comprise one type of such polymerizable compound, but may also contain a mixture of two or more chemically different polymerizable compounds of formula [1], for example differing in one or more of G, Z, or $R_1$. In addition, the polymerizable compound may be a mixture of chemically similar compounds, such as compounds having a different number of polymerizable groups, like from 1 to 10. For a single compound or molecule, n would be an integer; but for a mixture of compounds the number n represents an averaged value of the number of polymerizable groups per molecule (as can be calculated based on type and amount of starting materials used in the synthesis of the compounds, or be analytically determined). In embodiments, the composition comprises a polymerizable compound of formula [1] that has a functionality n of more than 1, for example of at least 1.1, to result in a certain degree of crosslinking in a cured coating. In embodiments, the polymerizable compound is multifunctional and has a functionality n of at least 1.2, 1.4, 1.6, 1.8, 1.9 or 2.0. In embodiments, n is at most 8, 6, 4, 3 or 2.5. In other embodiments, n is about 1.8-3, or preferably about 1.8-2.2.

The polymerizable compound contains group G, which is a residue of a hydrophobic hydroxy-functional oligomer. Without wishing to be bound to any theory, the inventor hypothesized that hydrophobicity of G and of the polymerizable compound, likely together with presence of urethane (and/or urea) linkages, plays an important role in the cured coating showing interaction with and adhesion to the surface of a substrate. This oligomer typically has a (number average) molar mass Mn of about 200-8000 g/mol. In embodiments, the oligomer has a molar mass Mn of at least 300, 500, or 700 g/mol. In other embodiments, molar mass Mn is at most 7000, 6000, 5000 or 4000 g/mol. Such molar mass ranges may affect the hydrophobic character of the compound of formula [1], and may provide a balance between solubility in the coating composition, affinity to the surface of a substrate, and degree of cross-linking of the composition upon curing. The molar mass of the oligomer can be determined using known methods; like GPC, for example using polystyrene standards and THF as solvent, or be calculated from its functionality n and the number of hydroxy endgroups per mass unit (which can be for example be determined by chemical analysis like titration).

The polymerizable compound contains group G, which is a residue of a hydroxy-functional hydrophobic oligomer that may be chosen from the group consisting of polyethers, polyesters, polycarbonates, polyurethanes, polyepoxides, polyamides, poly(meth)acrylamides, poly(meth)acrylates, polyolefins, or any combination thereof. In embodiments, the hydroxy-functional oligomer is a polyether, preferably a polyether that is not soluble in water. Examples of suitable polyethers include a polytetrahydrofuran, also called poly(tetramethylene ether), poly(tetramethylene oxide), or poly(1,4-butanediol), typically abbreviated as PTHF; or copolymers thereof, like a copolyether based on 1,4-butanediol and 2-methyl-1,4-butanediol, also referred to as a copolymer of tetrahydrofuran and methyl tetrahydrofuran, and typically abbreviated as PTGL. In embodiments, the hydroxy-functional oligomer can also partly be present in the compound in the form of a dimer or trimer, for example by chain extension resulting from reaction of an oligomer having two hydroxyl groups with a diisocyanate compound during the synthesis of the polymerizable compound of formula [1].

In embodiments, the component (a) further comprises a polymerizable compound containing group G, which group is a residue of a hydrophobic amine-functional oligomer, wherein the hydrophobic oligomer has a functionality and may be chosen from a group of oligomers equivalent to that described above for a hydroxy-functional oligomer. This means that such polymerizable compound contains a urea bond and can be represented by formula [1a]. Herein each $R_1$ and Z can be independently the same as is described herein for the compound of formula [1]. In further embodiments, the component (a) comprises or consists of a mixture of compounds of formula [1] and [1a], wherein the amount of latter compound is at most 80, 60, 40, 20, 10 or 5 mass % based on total components (a). In another embodiment, the component (a) (substantially) consists of compounds of formula [1a].

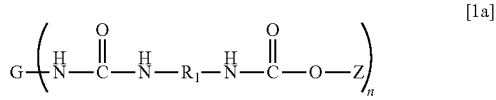

[1a]

In the polymerizable compound of formula [1], each $R_1$ independently is a residue of a $C_6$-$C_{20}$ aliphatic, cycloaliphatic, or aromatic hydrocarbon compound. $R_1$ typically resulted from synthesizing the polymerizable compound from a hydroxy-functional oligomer, a diisocyanate compound, and a (hydroxy functional) compound having a polymerizable group. In embodiments, each $R_1$ is such residue originating from a diisocyanate compound selected from the group consisting of 4,4'-diphenylmethane diisocyanate (MDI), 2,4-toluene diisocyanate, 2,6-toluene diisocyanate (TDI), 1,4-phenylene diisocyanate, hexamethylene diisocyanate (HDI), tetramethylene-1,4-diisocyanate, cyclohexane-1,4-diisocyanate, dicyclohexylmethane-4,4'-diisocyanate (HMDI), or isophorone diisocyanate (IPDI. In other embodiments, each $R_1$ independently is a residue of 2,4-toluene, 2,6-toluene, hexane, butane, cyclohexane, or isophorone. In other embodiments, each $R_1$ is a residue of TDI, HDI or IPDI.

In the polymerizable compound of formula [1], Z is a moiety having a polymerizable group. As polymerizable group any group that will react under influence of radiation and in presence of a photo-initiator with other similar groups to form an oligomer or polymer, for example via a radically induced addition reaction, and as known to a skilled person, may be used. A suitable polymerizable group, activated by the photo-initiator, may also co-react with the hydrophilic polymer present in the coating composition to form a graft on said polymer and/or to cross-link the polymer. The skilled person will be able to select a suitable group based on general knowledge. In embodiments, the polymerizable group is an unsaturated group, and may be selected from olefinic groups, styrenic groups, or (meth)acrylic groups. The polymerizable compound of formula [1] may also be a mixture of compounds having different moieties Z, that is having different polymerizable groups. Moiety Z, forming part of the polymerizable compound of formula [1] can for example be the result of reacting at least one hydroxy-functional compound having a polymerizable group with an isocyanate group of $R_1$.

In embodiments, Z of the polymerizable compound of formula [1] is a moiety having a (meth)acrylic group. In further embodiments, Z is a (meth)acrylic compound of formula [2], wherein each $R_2$ independently is a $C_1$-$C_{10}$ alkyl, and each $R_3$ independently is hydrogen or methyl.

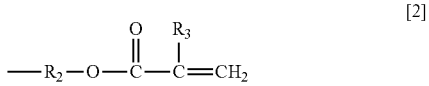

[2]

In further embodiments, Z is a moiety of formula [2], wherein each $R_3$ is hydrogen; i.e. Z comprises an acrylate group. In other embodiments, each $R_2$ independently is a $C_2$-$C_4$ alkyl. In embodiments, each $R_2$ is ethyl or propyl. In other embodiments, each $R_2$ is ethyl.

In embodiments, the polymerizable compound of formula [1] typically has a number average molar mass weight (Mn) of at least 500 g/mol, or at least 750, or 1000 g/mol. Generally the polymerizable compound has Mn of at most 100000 g/mol, or at most 50000, 25000, 10000, 6000, or even at most 4000 g/mol. Polymerizable compounds with molar mass within such ranges may result in a cured coating with a favorable cross-link density, i.e. properly balancing water swellability (to provide lubricity) and mechanical robustness (wear resistance and adhesion).

In embodiments, the polymerizable compound of formula [1] is soluble in a relatively polar solvent, but is not soluble or has only very limited solubility in water. Within the context of the disclosure this means that at least 1 g, preferably at least 2, 3, 4 or 5 g, of polymerizable compound of formula [1] can be dissolved in 100 g of the solvent of the coating composition at 25° C.

In embodiments, the polymerizable compound of formula [1] can be made by reacting a hydroxy-functional oligomer with a diisocyanate and a hydroxy-functional compound having a polymerizable group. Such reactions are known in the art, and a skilled person will be able to select suitable procedures and conditions to perform such synthesis. For example, hydroxy-functional oligomer may first be reacted with a diisocyanate with a molar ratio of isocyanate to hydroxy groups of 2, followed by reacting the remaining isocyanate groups with a hydroxy-functional compound having a polymerizable group. If statistical chain extension of the oligomer is not desired, reaction may be performed with a molar excess of diisocyanate, which excess can be removed, for example by distilling, before reacting with said compound having a polymerizable group. In an exemplary embodiment, the polymerizable compound according to formula [1] is the reaction product of a copolyether diol based on tetrahydrofuran or based on tetrahydrofuran and methyl tetrahydrofuran, toluene diisocyanate and hydroxyethyl acrylate.

The photo-curable coating composition, suitable for making a hydrophilic coating that can become lubricious upon wetting, comprises a polymerizable compound of formula [1], which may be present in an amount of about 2.0-30 mass % based on total dry mass of the composition; that is based on the sum of the mass of components a), b), c) and d), excluding the solvent component e). The amount based on total dry mass of the coating composition can alternatively be reported as based on the mass of dried and cured coating obtainable from the composition, which will be substantially the same.

In other embodiments, the component (a) in the composition may also be present at a relatively low amount of at least 0.5 mass %, although in such case curing time and/or amount of photo-initiator may need to be increased to obtain satisfactory performance of the coating on a substrate. In such embodiments therefore, the coating composition comprises the multifunctional polymerizable compound of formula [1] in an amount of at least 0.6, 0.7, 0.8, 0.9, 1.0, 1.2, 1.4, 1.5, or 1.8 mass % based on total dry mass of the composition.

In further embodiments, the coating composition comprises the multifunctional polymerizable compound of formula [1] in an amount of at least 2.5, 3.0. 3.5, 4.0, 4.5, 5.0, 5.5 or 6.0 mass % based on total dry mass of the composition. In other embodiments, the coating composition comprises the multifunctional polymerizable compound of formula [1] in an amount of at most 25, 20, 15, 12 or 10 mass % based on total dry mass of the composition.

Hydrophilic Polymer

The coating composition for making a hydrophilic coating comprises at least one hydrophilic polymer as component (b). Herein a hydrophilic polymer is understood to be a high molar mass, linear or branched polymer, which shows affinity for water and other polar liquids, and may be soluble in water. The hydrophilic polymer as such will attract and/or absorb water, also when present in a cured coating on a surface. The hydrophilic polymer capable of providing hydrophilicity to a coating may be a natural, synthetic or bio-derived polymer, and can be a copolymer, or a mixture of two or more such (co)polymers. The hydrophilic polymer is soluble in the (generally polar organic) solvent of the coating composition, and is typically a non-ionic polymer. The hydrophilic polymer may be at least one polymer selected from the group consisting of poly(lactams), like polyvinylpyrollidone, polyurethanes, copolymers of (meth)acrylates and (meth)acrylic acid, polyvinylalcohols, polyvinylethers, polyethyleneimines, polyethyleneoxides, polyamides, polyanhydrides, polyphosphazenes, cellulosics, for example carboxymethyl cellulose, hydroxymethyl cellulose, and hydroxypropylcellulose, heparin, dextran, polysacharrides, for example chitosan, hyaluronic acid, alginates, gelatin, and chitin, polyesters, for example polylactides, polyglycolides, and polycaprolactones, polypeptides, for example collagen, albumin, oligo peptides, polypeptides, short chain peptides, proteins, and oligonucleotides. Typically, the hydrophilic polymer does not comprise polymerizable groups like unsaturated groups, but the polymer may co-react with species formed from or by the photo-initiator and/or polymerizable compound of formula [1]. In embodiments, the hydrophilic polymer is susceptible to reaction with for example radicals generated by exposing the coating composition to radiation, to result in a certain agree of crosslinking; which crosslinking will still allow the hydrophilic polymer to absorb water, but will reduce or even prevent the polymer from being extracted from the coating during use, for example when present on the surface of a medical device exposed to an aqueous medium. Generally, the hydrophilic polymer has a molar mass Mn in the range of about 8 to 5000 kg/mol. In embodiments, molar mass is about 20-3000, or 200-2000 kg/mol. Molar mass (Mn) may be determined using common techniques like GPC or light scattering.

In embodiments, the hydrophilic polymer in the coating composition is a polyvinylpyrrolidone (PVP) or a polyethylene oxide. In further embodiments, the hydrophilic polymer is PVP or a copolymer thereof. For PVP and polymers of the same class, a K-value is typically used as indication of its molar mass. The K-value is determinable by Method W1307, Revision 5/2001 of the Viscotek Y501 automated relative viscometer; a manual may be found at www.ispcorp.com/products/hairscin/index_3.html. In embodiments, the PVP has a molar mass corresponding to at least K15, or at least K30 or K80 is preferred. In further embodiments, PVP of at least K90 and at most K120 is applied in the coating composition.

In alternative embodiments, the coating composition may optionally comprise, in addition to the non-ionic hydrophilic polymer, at least one ionic or ionizable hydrophilic polymer, also called polyelectrolyte. Herein a polyelectrolyte is understood to be a high molar mass linear or branched polymer wherein 5-100% of its monomer units contain an ionizable group; or ionized group when the polyelectrolyte is in an aqueous medium of suitable pH. Herein ionizable is understood to mean not (fully) ionized in neutral aqueous solutions, i.e. solutions having a pH between 6 and 8; but ionizable by changing conditions like pH. Presence of a polyelectrolyte in a coating composition may improve lubricity and dry-out time of the wetted hydrophilic coating. Herein dry-out time is defined as the period during which a hydrophilic coating remains lubricious in the open air after a device comprising the hydrophilic coating has been taken out of a wetting fluid wherein it had been stored and/or wetted. Hydrophilic coatings with an improved or longer dry-out time will have a lower tendency to lose water and to dry, prior to insertion into a patient's body, or in the body when it comes in contact with e.g. a mucous membrane or vein; which may lead to complications and/or damaging of tissue during maneuvering the device in the body. Considerations when selecting a suitable polyelectrolyte are its solubility and viscosity in aqueous media versus the solvent used in present coating composition, in addition to e.g. its biocompatibility. A polyelectrolyte with a relatively high molar mass is preferred for increasing the dry-out time, and also will show reduced tendency to migrate from the coating. Molar mass (Mn) is thus preferably at least 20, 50 or 100 kg/mol, and less than 1000, 500 or 300 kg/mol for handleability and solubility.

Examples of ionizable (or ionized) groups that may be present in the polyelectrolyte are ammonium groups, phosphonium groups, sulfonium groups, carboxylate groups, sulfate groups, sulfinic groups, sulfonic groups, phosphate groups, and phosphonic groups. Such groups are very effective in binding water. The polyelectrolyte may also comprise metal ions like alkali metal ions, such as $Na^+$, $Li^+$, or $K^+$, or alkaline earth metal ions, such as $Ca^{2+}$ and $Mg^{2+}$. In particular when the polyelectrolyte comprises quaternary amine salts, for example quaternary ammonium groups, anions may be present. Such anions can for example be halogenides, such as $Cl^-$, $Br^-$, $I^-$ and $F^-$, and also sulphates, nitrates, carbonates and phosphates.

Suitable polyelectrolytes are for example salts of homo- and co-polymers of acrylic acid, salts of homo- and co-polymers of methacrylic acid, salts of homo- and co-polymers of maleic acid, salts of homo- and co-polymers of fumaric acid, salts of homo- and co-polymers of monomers comprising sulfonic acid groups, homo- and co-polymers of monomers comprising quaternary ammonium salts and mixtures and/or derivatives thereof. Examples of suitable polyelectrolytes are poly(acrylamide-co-acrylic acid) salts, for example poly(acrylamide-co-acrylic acid) sodium salt, poly (acrylamide-co-methacrylic acid) salts, for example poly (acrylamide-co-methacrylic acid) sodium salt, poly(methacrylamide-co-acrylic acid) salts, for example poly (methacrylamide-co-acrylic acid) sodium salt, poly (methacrylamide-co-methacrylic acid) salts, for example poly(methacrylamide-co-methacrylic acid) sodium salt poly (acrylic acid) salts, for example poly(acrylic acid) sodium salt, poly(methacrylic acid) salts, for example poly(methacrylic acid) sodium salt, poly(acrylic acid-co-maleic acid) salts, for example poly(acrylic acid-co-maleic acid) sodium salt, poly(methacrylic acid-co-maleic acid) salts, for example poly(methacrylic acid-co-maleic acid) sodium salt, poly(acrylamide-co-maleic acid) salts, for example poly (acrylamide-co-maleic acid) sodium salt, poly(methacrylamide-co-maleic acid) salts, for example poly(methacrylamide-co-maleic acid) sodium salt, poly(acrylamido-2-methyl-1-propanesulfonic acid) salts, poly(4-styrene sulfonic acid) salts, poly(acrylamide-co-dialkyl ammonium chloride), quaternized poly[bis-(2-chloroethyl)ether-alt-1,3-bis[3-(dimethylamino)propyl[urea], polyallylammonium phosphate, poly(diallyldimethylammonium chloride), poly (sodium trimethyleneoxyethylene sulfonate), poly(dimethyldodecyl(2-acrylamidoethyl) ammonium bromide), poly (2-N methylpyridiniumethylene iodine), polyvinylsulfonic acids, and salts of poly(vinyl)pyridines, polyethyleneimines, and polylysines.

Particularly suitable polyelectrolytes for use in the current (non-aqueous) composition are copolymeric polyelectrolytes, which may be random or block copolymers, wherein said copolymeric polyelectrolyte is a copolymer comprising at least two different types of monomer units, wherein at least one type of units comprises ionizable or ionized groups and at least one type of constitutional units is absent of ionizable or ionized groups. An example of such a copolymeric polyelectrolyte is a poly(acrylamide-co-acrylic acid) salt.

It is noted that an ionic or ionizable polymer may also function as osmolality-increasing component; similarly as a low molar mass ionic or ionizable compound like sodium chloride.

In case the coating composition comprises a polyelectrolyte, the concentration thereof will be relatively low, and at least lower than that of the hydrophilic polymer. In embodiments, the coating composition comprises a polyelectrolyte, with a mass ratio of non-ionic hydrophilic polymer to polyelectrolyte from 99:1 to 60:40, or from 95:5 to 75:25.

The amount of hydrophilic polymer in the coating composition may vary widely, also dependent on other components. Generally, the amount of hydrophilic polymer is at least 10, 20, 30, 40, 50, 60, 70, or 80 mass % and at most 97, 95, 93, 92, 91, or 90 mass %, based on dry mass of the composition.

Photo-Initiator

The coating composition for making a hydrophilic coating comprises at least one photo-initiator as component (c). In the coating composition a Norrish type I and/or a Norrish type II initiator may be applied. Both types are free radical generating photo-initiators but are distinguished by the process that forms the initiating radicals. Compounds that undergo unimolecular bond cleavage upon irradiation to generate radicals are termed Norrish type I or homolytic photo-initiators. The Norrish type II photo-initiators generate radicals indirectly; by hydrogen abstraction from a suitable synergist, which may be a low molar mass compound or a polymer.

Examples of suitable Norrish Type I or free-radical photo-initiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Commercial examples of suitable Norrish Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly {2-hydroxy-2-methyl-1-[4-(1-methylvinyl)phenyl]propan-1-one}, Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethylbenzoyldi-phenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis (2,4,6-trimethylbenzoyl)-phenyl-phosphine-oxide, Ciba-Geigy), Irgacure 1700 (25:75% blend of bis (2,6-dimethoxybenzoyl)2,4,4-trimethyl-pentyl phosphine oxide and 2-hydroxy-2-methyl-1-phenyl-propan-1-one, Ciba-Geigy), and the like. Also mixtures of type I photo-initiators can be used.

Examples of Norrish Type II photo-initiators that can be used in the coating composition according to the invention include aromatic ketones such as benzophenone, xanthone, derivatives of benzophenone (e.g. chlorobenzophenone), substituted benzophenones blends of benzophenone, and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photoinitiators. Further examples include 2-benzoyl benzoic acid, 3-benzoyl benzoic acid, 4-benzoyl benzoic acid, 3,3',4, 4'-benzophenone tetracarboxilic acid, 4-benzoyl-N,N,N,-trimethylbenzene-methaminium chloride, 2-hydroxy-3-(4-benzoylphenoxy)-N,N,N-trimethyl-1-propanaminium chloride, 2-hydroxy-3-(3,4-dimethyl-9-oxo-9H-thioxanthon-2-yloxy)-N,N,N-trimethyl-1-propan-aminium chloride, thioxanthone-3-carboxylic acid, thioxanthone-4-carboxylic acid, anthraquinone 2-sulfonic acid, 9,10-anthraquinone-2,6-disulphonic acid, anthraquinone-2-sulfonic acid, anthraquinone-2-carboxylic acid and salts of these derivatives such as the sodium-, potassium-, calcium-, magnesium, iron-, copper and zinc salts.

In embodiments, the coating composition contains a Norrish Type II photo-initiator. Presence of such initiator may be advantageous, as such compound can also induce cross-linking of a polymer like PVP, in addition to initiating polymerization of the polymerizable compound of formula [1].

In further embodiments, the coating composition contains a mixture of Norrish Type I and Norrish Type II photo-initiator. If a mixture is applied, the mass ratio of Norrish type I photo-initiator to Norrish type II photo-initiator typically is between 10:1 and 1:10. In embodiments, said mass ratio is between 7:1 and 1:7 or between 5:1 and 1:5; preferably between 2:1 and 1:2.

In embodiments, the amount of photo-initiator in the coating composition may be from 0.2 to 5 mass %, based on dry mass. In other embodiments, the amount of photo-initiator in the coating composition is at least 0.3, 0.4 or 0.5 mass % and at most 4.5, 4.0, 3.5 or 3.0 mass %, based on dry mass of the composition.

Further Components

The coating composition for making a hydrophilic coating may optionally comprise at least one further component (or additive) as component (d), in addition to components (a)-(c) as described above. Examples of further components include a hydrophilic polymerizable compound (thus different from a component (a)); a low molar mass osmolality-increasing component such as urea, glycerol or an ionic or ionizable compound like sodium chloride. Other examples include one or more customary additives like a surfactant; an antioxidant; a radical stabilizer; a UV absorber; a light stabilizer; a heat polymerization inhibitor; a (silane) coupling agent; a coating surface improver; a leveling agent; a colorant, for example a pigment or a dye; a preservative; a plasticizer; a lubricant; a filler; a wettability improver; or a chain transfer agent. Most of such additive compounds are typically applied at relatively low concentrations, like 0.01-3 mass % based on total dry mass of the coating composition.

In embodiments, the coating composition comprises a surfactant as a component (d). A surfactant may for example improve spreading of the coating composition over the surface of a substrate and/or surface properties of the applied and cured coating. Generally, a surfactant is a surface-active agent comprised of a hydrophobic portion, usually a long alkyl chain, attached to a hydrophilic or water solubility enhancing functional group. Surfactants can be categorized according to charge present in the hydrophilic portion of the molecule (after dissociation in aqueous medium): ionic surfactants, for example anionic or cationic surfactants, and non-ionic surfactants. Examples of ionic surfactants include sodium dodecylsulfate (SDS), sodium cholate, bis(2-ethylhexyl)sulfosuccinate sodium salt, cetyltrimethylammoniumbromide (CTAB), lauryldimethylamine-oxide (LDAO), N-laurylsarcosine sodium salt and sodium deoxycholate (DOC). Examples of non-ionic surfactants include alkyl polyglucosides such as Triton™ BG-10 Surfactant and Triton CG-110 Surfactant, branched secondary aAlcohol eEthoxylates such as Tergitol™ TMN Series, ethylene oxide/propylene oxide copolymers, such as Tergitol L Series, and Tergitol XD, XH, and XJ Surfactants, nonylphenol ethoxylates such as Tergitol NP Series, octylphenol ethoxylates, such as Triton X Series, secondary alcohol ethoxylates, such as Tergitol 15-S Series and specialty alkoxylates, such as Triton CA Surfactant, Triton N-57 Surfactant, Triton X-207 Surfactant, Tween 80 (polyethylene glycol sorbitan monooleate; with about 80 ethylene oxide units) and Tween 20 (polyethylene glycol sorbitan monolaurate; with about 20 ethylene oxide units). If used, surfactant is typically applied at relatively low concentration, for example 0.1-2 mass % based on the total mass of the dry coating.

In embodiments, the coating composition also comprises as a component (d) one or more further polymerizable compounds different from the polymerizable compound of formula [1], like a polymerizable compound of more hydrophilic character. This compound can be of low molar mass or be oligomeric, and may have on average one or more polymerizable groups like an olefinic, styrenic or (meth) acrylic unsaturated group. Suitable examples include multifunctional compounds having two or more polymerizable groups; often referred to as cross-linking monomers. Such compounds are well known to a person skilled in the art, and may be added to increase and/or control the cross-link density of a cured coating. Examples include various commercially available cross-linkers, like dimethacrylates, diacrylates, or diacrylamides. Other examples include oligomeric compounds like poly(ethylene oxide) diacrylate (PEG-DA) or poly(ethylene oxide) diacrylamide (PEG-DAA). If such compounds are present in the coating composition, their concentration may be at least 0.1, 1, 2 or 3 mass % and at most 30, 25, 20, 15, 10 or 5 mass %. In other embodiments, the concentration of such hydrophilic polymerizable compound is lower than that of the hydrophobic polymerizable compound of formula [1]; for example at most 80, 60, 40, 20 or 10 mass % of the mass of the hydrophobic polymerizable compound.

In embodiments, the component (d) is soluble in the solvent, and dissolved in the coating composition. The skilled person will realize that depending on the type of component (d), such component may also be dispersed in the composition as long as it does not negatively affect forming and curing of a coating layer from the coating composition.

Solvent

The coating composition for making a hydrophilic coating comprises at least one solvent as component (e), wherein the components (a( )-c, and optionally also (d)) can be homogeneously dissolved. Examples of suitable solvents are generally relatively polar organic liquids. In embodiments, the solvent is miscible to at least some extend with water. Examples of suitable solvents include $C_1$-$C_6$ alcohols, like methanol, ethanol, propanol, isopropanol, butanol, isobutanol, t-butanol; acetone; methylethyl ketone; tetrahydrofuran; and mixtures thereof. The solvent may also contain water, provided such mixed solvent can dissolve at least components (a)-(c) of the composition, preferably all components (a)-(d). In further embodiments, the solvent is at least one selected from methanol, ethanol, and isopropanol, including mixtures thereof or mixtures comprising some water, like 96% ethanol (comprising about 4% of water). In embodiments, the solvent or mixture of solvents has relatively high volatility, or a relatively low boiling point, for example of at most 150, 130, 120, 110 or 100° C., such that the solvent can quickly evaporate from a layer of coating composition applied to a substrate; allowing relatively fast solidification of the liquid composition and fast curing of the coating to result in short cycle times and an efficient and economic coating process.

The coating composition can contain a widely varying amount of solvent, which allows making a solution having a viscosity that is adjustable to use with different coating techniques. In other embodiments, the coating composition contains such amount of solvent that the solution has a relatively low viscosity, to enable applying thin coating layers via for example a dip-coating process on thin, elongated articles like catheters and guidewires.

In embodiments, the coating composition contains 40-99.5 mass % of solvent based on the total composition. In other embodiments, the coating composition contains at least 50, 60, 70, 80, 85, 90 mass % of solvent, and at most 99.0, 98.5, 98, 97.5, 97.0, 96.5, 96.0, 95.5 or 95.0 mass % of solvent.

In exemplary embodiments, the photo-curable coating composition comprises, based on total dry mass of the composition,
2.0-30 mass % of component (a);
97.8-30 mass % of component (b);
0.2-5 mass % of component (c); and
0-35 mass % of component (d);
and wherein the sum of (a)-(d) is 100%.

In other exemplary embodiments, the photo-curable coating composition comprises, based on total dry mass of the composition,
3.5-30 mass % of component (a);
96.3-30 mass % of component (b);
0.2-5 mass % of component (c); and
0-35 mass % of component (d);
and wherein the sum of (a)-(d) is 100%.

In other embodiments, the photo-curable coating composition comprises, based on total dry mass of the composition, 4-25 mass % of component (a); 95.2-46 mass % of component (b); 0.3-4 mass % of component (c); and 0.5-25 mass % of component (d); and wherein the sum of (a)-(d) is 100%.

In further embodiments, the photo-curable coating composition comprises, based on total dry mass of the composition, 5-20 mass % of component (a); 93.6-46 mass % of component (b); 0.4-3.5 mass % of component (c); and 1-20 mass % of component (d); and wherein the sum of (a)-(d) is 100%.

In other embodiments, the photo-curable coating composition comprises, based on total dry mass of the composition, 6-12 mass % of component (a); 91.5-75 mass % of component (b); 0.5-3 mass % of component (c); and 2-10 mass % of component (d); and wherein the sum of (a)-(d) is 100%.

In exemplary embodiments, the photo-curable coating composition has a kinematic viscosity, determined using an Ubbelohde viscometer at 25° C. as indicated in the experimental part, of about 5-200 mm$^2$/s (or cSt; centistoke). The viscosity of the coating composition is one of the variables that may be varied to affect the thickness of a coating layer applied to a substrate surface. In case of vascular applications like catheters, a relatively thin hydrophilic coating layer may be preferred. In embodiments, the coating composition therefore has a kinematic viscosity of about 5-50 mm$^2$/s; preferably at least 6, 8 or 10 and at most 40, 35, 30, or 25 mm$^2$/s. If a somewhat thicker hydrophilic coating layer is desired, like for example in case of intermittent catheters or Foley catheters, the coating the composition has a kinematic viscosity of 50-200 mm$^2$/s; preferably at least 60, 70, 80 90 or 100 mm$^2$/s and at most 450, 400, 350, 300 or 250 mm$^2$/s. The coating compositions are typically prepared using methods known in the art, for example by dissolving all components in a selected solvent under mild conditions.

In another aspect, the invention relates to a hydrophilic coating that is obtained by drying and curing a layer of the coating composition according to the invention.

In a further aspect, the invention relates to a lubricious hydrophilic coating that is obtained by drying and curing a layer of the coating composition according to the invention, and subsequently contacting the coating with a wetting agent.

A wetting agent is defined as a liquid composition, typically comprising water, which is used to wet a hydrophilic coating, for example by contacting the surface of a coating on a substrate, such that the coating will absorb a certain amount of one or more components of the wetting agent; to result in increased lubricity of the coating. In the art both oil-based and water-based wetting agents are described. In embodiments, a water-based or aqueous wetting agent is applied to wet the hydrophilic coating of present invention. Typically, such aqueous wetting agent may contain in addition to water one or more other components as known in the art; like compounds that lower surface tension and ease spreading of the wetting agent over the coating surface such as surfactants or other organic compounds soluble in water like higher alcohols or glycerol esters; compounds that stabilize the wetted coating like antioxidants such as vitamin E; compounds that serve to better retain water in the wetted hydrophilic coating like salts or urea; compounds to control pH like an organic or inorganic buffer; and/or antibiotics or antimicrobial compounds. Depending on the situation, the skilled person will be able to select a wetting agent of suitable composition, based on general knowledge and optionally some routine experiments.

A further aspect of the invention concerns a method of applying a hydrophilic and optionally lubricious coating to an article comprising steps of
  Applying a coating composition according to the invention as described herein above to at least a part of a surface of the article;
  At least partly removing the solvent from the applied coating composition;
  Curing the applied coating composition by exposing to UV-light during or after removing solvent to form a hydrophilic coating; and
  optionally contacting the hydrophilic coating with a wetting agent to form a lubricious coating.

In this method, the coating composition may be applied to a surface using known techniques in the art, like dip-coating, spray coating, wash coating, vapor deposition, or by using a brush or roller; for example dependent on the type of article. For elongated and relatively thin articles like guidewires and catheters dip-coating may be the preferred application technique. The article may have a range of geometries, including films, sheets, rods, tubes, molded parts of regular or irregular shape, fibers, and fabrics; and can have a surface that is made from different materials and have different textures, like a porous, non-porous, smooth, rough, even or uneven surface. It is an advantage of present coating composition that, in most cases, it can be applied directly to the said surfaces, which are preferably cleaned but need no chemical pretreatment of primer coating. Therefore, the process typically does not comprise a step of chemically pretreating or applying a primer composition to the surface to be coated before applying the coating composition of the invention.

The thickness of the layer of coating composition applied, and of the hydrophilic coating after drying and curing, may be controlled by altering coating parameters like the soaking time, pull-up speed, or viscosity of the hydrophilic coating formulation and the number of coating steps. Typically the thickness of a dry hydrophilic coating on a surface of an article ranges from 0.1-300 m, preferably at least 0.2, 0.3, 0.4, 0.5 m, and preferably at most 200, 100, 50, 40, 30, 20 or 15 m.

In the method, the step of photo curing comprises exposing the article to a suitable radiation source, like UV lamps, during a time sufficient to substantially react the polymerizable compounds in the coating. The skilled person will be able select suitable conditions like intensity and wavelength of radiation and exposing time, depending on type of photoinitiator and based on general knowledge and some experiments. Generally, exposing or curing time will be from about 5, 10, 20, and up to about 50, 100, 250 or 500 seconds, depending on the type and energy of the radiation source that is used.

In the optional step of contacting the hydrophilic coating with a wetting agent to form a lubricious coating, the wetting agent may be a composition as known in the art for such purpose. In embodiments the wetting is an aqueous wetting agent as described herein above.

Another aspect of the invention relates to an article like a medical device having on at least part of its surface a single-layer, hydrophilic, and optionally lubricious coating, which article is obtained by the method of the invention.

In embodiments, said medical device has a single-layer hydrophilic coating, which coating shows after wetting a lubricity of at most 15 g, determined as the averaged friction with the method described in the experimental part using a Harland Friction Tester FTS 6000. In other embodiments, the medical device has a single-layer hydrophilic coating, which coating shows after wetting a lubricity of at most 14, 13, 12, 11, 10, 9, 8, or 7 g.

Examples of articles that can benefit from having such coating according to present invention include substrates used in the study of living cells and systems, including diagnostic, therapeutic, and experimental human medicine, veterinary medicine, and agricultural fields. Other articles include medical devices for diagnostic and/or therapeutic purposes; including cardiovascular devices, neurovascular devices, peripheral vascular devices, devices for use in the urinary-tract, and devices for use in ophthalmology, orthopedics, surgery and the like. Examples include catheters, guidewires, stents, delivery devices for e.g. heart valve prosthesis or intraocular lenses, contact lenses, implantable devices, extracorporeal devices, and tools and instruments. Articles that particularly benefit from having applied on at least part of the surface a hydrophilic and optionally lubricious coating of the invention include medical devices or components such as intermittent catheters, balloon catheters, PTCA catheters, stent delivery catheters, introducer sheaths, guide wires, stents, syringes, metal and plastic implants, contact lenses and medical tubing. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of a range of values herein is merely intended to serve as a shorthand method of referring individually to each separate value falling within the range, and each separate value is incorporated into the specification as if it were individually recited herein. The use of any and all examples, or exemplary language (e.g., "such as" or "like") provided herein, is intended merely to better illustrate the invention and does not pose a limitation on the scope of the invention unless otherwise claimed. No language in the specification should be construed as indicating any non-claimed element as essential to practicing the invention.

Preferred embodiments of the inventions are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the inventions to be practiced otherwise than as specifically described herein. Accordingly, the inventions include all modifications and equivalents of the subject matter recited in the claims appended hereto as permitted by applicable law. While certain optional features are described as embodiments of the inventions, the description is meant to encompass and specifically disclose all combinations of these embodiments unless specifically indicated otherwise or physically impossible.

Various aspects, embodiments and ways of performing the invention as described above, are hereafter further summarized by a series of exemplary embodiments.

[1] A photo-curable coating composition, which is suitable for making a hydrophilic coating, which composition comprises components
   (a) A polymerizable compound of formula [1],
      wherein G is a residue of a hydrophobic hydroxy-functional oligomer; n is 1-10, each $R_1$ independently is a residue of a $C_6$-$C_{20}$ aliphatic, cycloaliphatic, or aromatic hydrocarbon compound, and Z is a moiety having a polymerizable group;

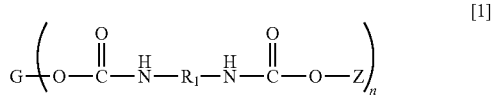

[1]

(b) A hydrophilic polymer;
   (c) A photo-initiator;
   (d) Optionally one or more further components, and
   (e) A solvent for components (a)-(c).

[2] The composition of embodiment 1, wherein component (a) is present in an amount of 0.5-30 mass % based on total dry mass of the composition.

[3] The composition of embodiment 2, wherein component (a) is present in an amount of at least 0.6, 0.7, 0.8, 0.9, 1.0, 1.2, 1.4, 1.5, or 1.8 mass % based on total dry mass of the composition.

[4] The composition of embodiment 1, wherein component (a) is present in an amount of 2.0-30 mass % based on total dry mass of the composition.

[5] The composition of any one of embodiment 1-4, wherein the composition comprises one type of polymerizable compound of formula [1].

[6] The composition of any one of embodiment 1-4, wherein the composition comprises a mixture of two or more chemically different polymerizable compounds of formula [1], for example differing in one or more of G, Z, or $R_1$.

[7] The composition of any one of embodiment 1-4, wherein the composition comprises a mixture of chemically similar compounds of formula [1] that differ in number of polymerizable groups, preferably n has an average value of from 1 to 10.

[8] The composition of any one of embodiment 1-7, wherein component (a) further comprises a polymerizable compound that contains a group G, which is a residue of a hydrophobic amine-functional oligomer.

[9] The composition of any one of embodiments 1-8, wherein the composition comprises a polymerizable compound of formula [1] that has a functionality n of more than 1, preferably a functionality n of at least 1.1, 1.2, 1.4, 1.6, 1.8, 1.9 or 2.0 and of at most 8, 6, 4, 3 or 2.5.

[10] The composition of embodiment [5], wherein the functionality n is about 1.8-3, or about 1.8-2.2.

[11] The composition of any one of embodiments 1-10, wherein the group G is a residue of at least one hydrophobic oligomer having a (number average) molar mass Mn of about 200-8000 g/mol, preferably the oligomer has a molar mass Mn of at least 300, 500, or 700 g/mol and of at most 7000, 6000, 5000 or 4000 g/mol.

[12] The composition of any one of embodiments 1-11, wherein the group G is a residue of at least one hydrophobic oligomer chosen from the group consisting of polyethers, polyesters, polycarbonates, polyurethanes, polyepoxides, polyamides, poly(meth)acrylamides, poly(meth)acrylates, and polyolefins.

[13] The composition of any one of embodiments 1-12, wherein the group G is a residue of a polyether oligomer, preferably of a polyether oligomer that is not soluble in water, like a polytetrahydrofuran or a copolymer thereof, like a copolyether based on 1,4-butanediol and 2-methyl-1, 4-butanediol.

[14] The composition of any one of embodiments 1-13, wherein the group G is a residue of a hydrophobic oligomer that is at least partly present in the form of a dimer or trimer, for example resulting from reaction of an oligomer having two hydroxyl groups with a diisocyanate.

[15] The composition of any one of embodiments 1-14, wherein each $R_1$ independently is a residue of a $C_6$-$C_{20}$ aliphatic, cycloaliphatic, or aromatic hydrocarbon compound.

[16] The composition of any one of embodiments 1-15, wherein $R_1$ resulted from synthesizing the polymerizable compound of formula [1] from a hydroxy-functional oligomer, a hydroxy functional compound having a polymerizable group, and a diisocyanate compound OCN—$R_1$—NCO.

[17] The composition of embodiment 16, wherein the diisocyanate compound is at least one selected from the group consisting of 4,4'-diphenylmethane diisocyanate (MDI), 2,4-toluene diisocyanate, 2,6-toluene diisocyanate (TDI), 1,4-phenylene diisocyanate, hexamethylene diisocyanate (HDI), tetramethylene-1,4-diisocyanate, cyclohexane-1,4-diisocyanate, dicyclohexylmethane-4,4'-diisocyanate (HMDI), and isophorone diisocyanate (IPDI).

[18] The composition of any one of embodiments 1-17, wherein each $R_1$ independently is at least one residue selected from the group consisting of 2,4-toluene, 2,6-toluene, hexane, butane, cyclohexane, and isophorone.

[19] The composition of any one of embodiments 1-18, wherein each $R_1$ is residue of TDI, HDI or IPDI.

[20] The composition of any one of embodiments 1-19, wherein Z has a polymerizable group that reacts under influence of radiation and in presence of a photo-initiator with other similar groups to form an oligomer or polymer, preferably via a radically induced addition reaction.

[21] The composition of any one of embodiments 1-20, wherein Z has a polymerizable group that when activated by the photo-initiator co-reacts with the hydrophilic polymer present in the coating composition to form a graft on said polymer and/or to cross-link said polymer.

[22] The composition of any one of embodiments 1-21, wherein Z has an unsaturated polymerizable group, preferably chosen from the group consisting of olefinic groups, styrenic groups, and (meth)acrylic groups.

[23] The composition of any one of embodiments 1-22, wherein Z has a (meth)acrylic group.

[24] The composition of any one of embodiments 1-23, wherein Z resulted from reacting a hydroxy-functional compound having a polymerizable group with an isocyanate group of $R_1$.

[25] The composition of any one of embodiments 1-24, wherein Z is a (meth)acrylic moiety of formula [2], wherein each $R_2$ independently is a $C_1$-$C_{10}$ alkyl, and each $R_3$ independently is hydrogen or methyl.

[26] The composition of embodiment 25, wherein Z is a moiety of formula [2], wherein each $R_3$ is hydrogen.

[27] The composition of embodiment 25 or 26, wherein Z is a moiety of formula [2], wherein each $R_2$ independently is a $C_2$-$C_4$ alkyl, preferably each $R_2$ is ethyl or propyl, or each $R_2$ is ethyl.

[28] The composition of any one of embodiments 1-27, wherein the polymerizable compound of formula [1] has a number average molar mass (Mn) of 500-100000 g/mol, preferably of at least 750 or 1000 g/mol and at most 50000, 25000, 10000, 6000, or 4000 g/mol.

[29] The composition of any one of embodiments 1-28, wherein the polymerizable compound of formula [1] is soluble in a relatively polar solvent, but is not or poorly soluble in water.

[30] The composition of any one of embodiments 1-29, wherein the polymerizable compound of formula [1] has been made by reacting a hydroxy-functional oligomer with a diisocyanate and a hydroxy-functional compound having a polymerizable group.

[31] The composition of any one of embodiments 1-30, wherein the polymerizable compound of formula [1] has been made by first reacting a hydroxy-functional oligomer with a diisocyanate at a molar ratio of isocyanate to hydroxy groups of 2, followed by reacting the remaining isocyanate groups with a hydroxy-functional compound having a polymerizable group.

[32] The composition of any one of embodiments 1-30, wherein the polymerizable compound of formula [1] has been made by first reacting a hydroxy-functional oligomer with a molar excess of diisocyanate, followed by removing non-reacted diisocyanate, and then reacting the remaining isocyanate groups with a hydroxy-functional compound having a polymerizable group.

[33] The composition of any one of embodiments 1-32, wherein the polymerizable compound according to formula [1] is the reaction product of a copolyether diol based on tetrahydrofuran or based on tetrahydrofuran and methyl tetrahydrofuran, toluene diisocyanate and hydroxyethyl acrylate.

[34] The composition of any one of embodiments 1-33, wherein the polymerizable compound of formula [1] is present in an amount of at least 2.5, 3.0, 3.5, 4.0, 4.5, 5.0, 5.5 or 6.0 mass % based on total dry mass of the composition.

[35] The composition of any one of embodiments 1-34, wherein the polymerizable compound of formula [1] is present in an amount of at most 30, 25, 20, 15, 12 or 10 mass %, based on total dry mass of the composition.

[36] The composition of any one of embodiments 1-35, wherein the coating composition comprises at least one hydrophilic polymer as component (b), which polymer is a linear or branched polymer; a homopolymer or copolymer; a natural, bio-derived or synthetic polymer; of a blend thereof.

[37] The composition of any one of embodiments 1-36, wherein the hydrophilic polymer is a non-ionic polymer that is soluble in the (organic) solvent of the coating composition.

[38] The composition of any one of embodiments 1-37, wherein the hydrophilic polymer is at least one polymer selected from the group consisting of polylactams, polyurethanes, copolymers of (meth)acrylates and (meth)acrylic acid, polyvinylalcohols, polyvinylethers, polyethyleneimines, polyethyleneoxides, polyamides, polyesters, polyanhydrides, polyphosphazenes, cellulosics, heparins, dextrans, polysacharrides, alginates, gelatins, polypeptides, proteins, and oligonucleotides.

[39] The composition of any one of embodiments 1-38, wherein the hydrophilic polymer has a molar mass Mn of about 8 to 5000 kg/mol, preferably molar mass is about 20-3000, or 200-2000 kg/mol.

[40] The composition of any one of embodiments 1-39, wherein the hydrophilic polymer is a polyvinylpyrrolidone (PVP) or a polyethylene oxide.

[41] The composition of any one of embodiments 1-40, wherein the hydrophilic polymer is PVP or a copolymer thereof, preferably the PVP has a molar mass corresponding to at least K15, or at least K30 or K80.

[42] The composition of any one of embodiments 1-41, wherein the hydrophilic polymer is PVP or a copolymer thereof, having a molar mass corresponding to at least K90 and at most K120.

[43] The composition of any one of embodiments 1-42, wherein the coating composition further comprises a polyelectrolyte that is soluble in the (organic) solvent of the coating composition.

[44] The composition of embodiment 43, wherein the polyelectrolyte has a molar mass Mn of at least 20, 50 or 100 kg/mol, and less than 1000, 500 or 300 kg/mol.

[45] The composition of any one of embodiments 43-44, wherein the polyelectrolyte has ionizable or ionized groups, which may be selected from ammonium groups, phosphonium groups, sulfonium groups, carboxylate groups, sulfate groups, sulfinic groups, sulfonic groups, phosphate groups, and phosphonic groups.

[46] The composition of any one of embodiments 43-45, wherein the polyelectrolyte comprises metal ions, like alkali metal ions or alkaline earth metal ions.

[47] The composition of any one of embodiments 43-46, wherein the polyelectrolyte comprises anions, like halogenides, sulphates, nitrates, carbonates and phosphates.

[48] The composition of any one of embodiments 43-47, wherein the polyelectrolyte is a salt of homo- and co-polymers of acrylic acid, of homo- and co-polymers of methacrylic acid, of homo- and co-polymers of maleic acid, of homo- and co-polymers of fumaric acid, of homo- and co-polymers of monomers comprising sulfonic acid groups, of homo- and co-polymers of monomers comprising quaternary ammonium salts, or of mixtures and/or derivatives thereof.

[49] The composition of any one of embodiments 43-48, wherein the polyelectrolyte is a poly(acrylamide-co-acrylic acid) salt, a poly(acrylamide-co-methacrylic acid) salt, a poly(methacrylamide-co-acrylic acid) salt, a poly(methacrylamide-co-methacrylic acid) salt, a poly(acrylic acid) salt, a poly(methacrylic acid) salt, a poly(acrylic acid-co-maleic acid) salt, a poly(methacrylic acid-co-maleic acid) salt, a poly(acrylamide-co-maleic acid) salt, a poly(methacrylamide-co-maleic acid) salt, a poly(acrylamido-2-methyl-1-propanesulfonic acid) salt, a poly(4-styrene sulfonic acid) salt, a poly(acrylamide-co-dialkyl ammonium chloride), a quaternized poly[bis-(2-chloroethyl)ether-alt-1,3-bis[3-(dimethylamino)propyl[urea], a polyallylammonium phosphate, a poly(diallyldimethylammonium chloride), a poly(sodium trimethyleneoxyethylene sulfonate), a poly(dimethyldodecyl(2-acrylamidoethyl) ammonium bromide), a poly(2-N methylpyridiniumethylene iodine), a polyvinylsulfonic acid, a salt of a poly(vinyl)pyridine, polyethyleneimine salt, or a polylysine salt.

[50] The composition of any one of embodiments 43-49, wherein the polyelectrolyte is a copolymer, like a random or block copolymer comprising at least two different types of monomer units

[51] The composition of any one of embodiments 43-50, wherein the polyelectrolyte a copolymer comprising a monomer with ionizable or ionized groups and a monomer without ionizable or ionized groups, like a poly(acrylamide-co-acrylic acid) salt.

[52] The composition of any one of embodiments 43-51, wherein the polyelectrolyte is present at a concentration lower than that of the hydrophilic polymer.

[53] The composition of any one of embodiments 43-52, wherein a mass ratio of non-ionic hydrophilic polymer to polyelectrolyte is from 99:1 to 60:40, or from 95:5 to 75:25.

[54] The composition of any one of embodiments 1-53, wherein the hydrophilic polymer is present in an amount of at least 10, 20, 30, 40, 50, 60, 70, or 80 mass % and at most 97, 95, 93, 92, 91, or 90 mass %, based on dry mass of the composition.

[55] The composition of any one of embodiments 1-54, wherein the component (c) is at least one Norrish type I photo-initiator and/or at least one Norrish type II photo-initiator.

[56] The composition of any one of embodiments 1-55, wherein the photo-initiator is at least one Norrish Type I photo-initiator selected from the group consisting of benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, and halogenated acetophenone derivatives.

[57] The composition of any one of embodiments 1-56, wherein the photo-initiator is at least one Norrish Type II photo-initiator selected from the group consisting of aromatic ketones such as benzophenone, xanthone, derivatives of benzophenone (e.g. chlorobenzophenone), substituted benzophenones, blends of benzophenone, benzophenone derivatives (e.g. Photocure 81, a 50/50 blend of 4-methyl-benzophenone and benzophenone), Michler's Ketone, Ethyl Michler's Ketone, thioxanthone, xanthone derivatives like Quantacure ITX (isopropyl thioxanthone), benzil, anthraquinones (e.g. 2-ethyl anthraquinone), coumarin, and chemical derivatives these photoinitiators.

[58] The composition of any one of embodiments 1-57, wherein the photo-initiator is at least one Norrish Type II photo-initiator selected from the group consisting of 2-benzoyl benzoic acid, 3-benzoyl benzoic acid, 4-benzoyl benzoic acid, 3,3',4, 4'-benzophenone tetracarboxilic acid, 4-benzoyl-N,N,N,-trimethylbenzene-methaminium chloride, 2-hydroxy-3-(4-benzoylphenoxy)-N,N,N-trimethyl-1-propanaminium chloride, 2-hydroxy-3-(3,4-dimethyl-9-oxo-9H-thioxanthon-2-yloxy)-N,N,N-trimethyl-1-propanaminium chloride, thioxanthone-3-carboxylic acid, thioxanthone-4-carboxylic acid, anthraquinone 2-sulfonic acid, 9,10-anthraquinone-2,6-disulphonic acid, anthraquinone-2-sulfonic acid, anthraquinone-2-carboxylic acid, and salts of these derivatives.

[59] The composition of any one of embodiments 1-58, wherein the coating composition contains at least a Norrish Type II photo-initiator.

[60] The composition of any one of embodiments 1-59, wherein the coating composition contains a mixture of Norrish Type II and Norrish Type I photo-initiators, preferably at a mass ratio of Norrish type II photo-initiator to Norrish type I photo-initiator of between 10:1 and 1:10; between 7:1 and 1:7; between 5:1 and 1:5; or between 2:1 and 1:2.

[61] The composition of any one of embodiments 1-60, wherein the amount of photo-initiator in the coating composition is from 0.2 to 5 mass %, preferably the amount is at least 0.3, 0.4 or 0.5 mass % and at most 4.5, 4.0, 3.5 or 3.0 mass % (based on dry mass of the composition).

[62] The composition of any one of embodiments 1-61, wherein the composition comprises one or more further components as component (d), which may include a low molar mass osmolality-increasing component such as urea, glycerol, or an ionic or ionizable compound like sodium chloride; a surfactant; an antioxidant; a radical stabilizer; a UV absorber; a light stabilizer; a heat polymerization inhibitor; a coupling agent such as a silane compound; a coating surface improver; a leveling agent; a colorant such as a pigment or a dye; a preservative; a plasticizer; a lubricant; a filler; a wettability improver; or a chain transfer agent.

[63] The composition of embodiment 62, wherein each further component can be present at an amount of 0.01-3 mass % based on total dry mass of the composition.

[64] The composition of any one of embodiments 1-63, wherein the coating composition further comprises a surfactant as a component (d).

[65] The composition of embodiment 64, wherein the surfactant is an anionic or cationic surfactant.

[66] The composition of embodiment 65, wherein the ionic surfactant is a compound selected from the group consisting of sodium dodecylsulfate (SDS), sodium cholate, bis(2-ethylhexyl)sulfosuccinate sodium salt, cetyltrimethylammoniumbromide (CTAB), lauryldimethylamine-oxide (LDAO), N-laurylsarcosine sodium salt and sodium deoxycholate (DOC).

[67] The composition of embodiment 64, wherein the surfactant is a non-ionic surfactant.

[68] The composition of embodiment 67, wherein the surfactant is a compound selected from the group consisting of alkyl polyglucosides such as Triton™ BG-10 and Triton™ CG-110; branched secondary alcohol ethoxylates such as Tergitol™ TMN; ethylene oxide/propylene oxide copolymers such as Tergitol L and Tergitol XD, XH, and XJ; nonylphenol ethoxylates such as Tergitol NP; octylphenol ethoxylates such as Triton X; secondary alcohol ethoxylates such as Tergitol 15-S; specialty alkoxylates such as Triton CA, Triton N-57, Triton X-207; Tween 80 (polyethylene glycol sorbitan monooleate with about 80 ethylene oxide units); and Tween 20 (polyethylene glycol sorbitan monolaurate with about 20 ethylene oxide units).

[69] The composition of any one of embodiments 64-68, wherein the surfactant is present at an amount of 0.1-2 mass % based on the total mass of the dry coating.

[70] The composition of any one of embodiments 1-69, wherein the coating composition comprises as a component (d) one or more further polymerizable compounds different from the polymerizable compound of formula [1].

[71] The composition of embodiment 70, wherein the further polymerizable compound has a more hydrophilic character than the polymerizable compound of formula [1].

[72] The composition of embodiment 70 or 71, wherein the further polymerizable compound is oligomeric and has on average one or more polymerizable groups, like an olefinic, styrenic or (meth)acrylic unsaturated group.

[73] The composition of any one of embodiments 70-72, wherein the further polymerizable compound has two or more polymerizable groups.
[74] The composition of any one of embodiments 70-73, wherein the further polymerizable compound is a dimethacrylate, diacrylate, or diacrylamide.
[75] The composition of any one of embodiments 70-74, wherein the further polymerizable compound is a poly(ethylene oxide) diacrylate (PEG-DA) or a poly(ethylene oxide) diacrylamide (PEG-DAA)
[76] The composition of any one of embodiments 70-75, wherein the further polymerizable compound is present in an amount of at least 0.1, 1, 2 or 3 mass % and at most 25, 20, 15, 10, 5, 4, 3, 2 or 1 mass % based on total dry mass of the composition.
[77] The composition of any one of embodiments 70-76, wherein the further polymerizable compound is present at a lower amount than the polymerizable compound of formula [1]; preferably at an amount of at most 80, 60, 40, 20 or 10 mass % of the mass of the polymerizable compound of formula [1].
[78] The composition of any one of embodiments 1-77, wherein the coating composition comprises at least one solvent as component (e) wherein the other components (a)-(c) and optionally (d) can be dissolved and which solvent is at least to some extend miscible with water.
[79] The composition of any one of embodiments 1-78, wherein the solvents is a relatively polar organic liquid selected from $C_1$-$C_6$ alcohols like methanol, ethanol, propanol, isopropanol, butanol, isobutanol, t-butanol; acetone; methylethyl ketone; tetrahydrofuran; or a mixture thereof.
[80] The composition of any one of embodiments 1-79, wherein the solvent contains water.
[81] The composition of any one of embodiments 1-80, wherein the solvent is at least one selected from methanol, ethanol, and isopropanol; including mixtures thereof or mixtures comprising some water, like 96% ethanol.
[82] The composition of any one of embodiments 1-81, wherein the coating composition contains 40-99.5 mass % of solvent.
[83] The composition of any one of embodiments 1-82, wherein the coating composition contains at least 50, 60, 70, 80, 85, 90 or 95 mass % of solvent, and at most 99.0, 98.5, 98, 97.5 or 97.0 mass % of solvent.
[84] The composition of any one of embodiments 1-83, wherein the coating composition contains such an amount of solvent that the solution has a relatively low viscosity, enabling application of thin coating layers via for example a dip-coating process on thin, elongated articles like catheters and guidewires.
[85] The composition of any one of embodiments 1-84, wherein the coating composition has a kinematic viscosity, determined using an Ubbelohde viscometer at 25° C., of about 5-200 mm$^2$/s, preferably kinematic viscosity is at least 6, 8 or 10 and at most 450, 400, 350, 300 or 250 mm$^2$/s.
[86] The composition of any one of embodiments 1-85, wherein the coating composition has a kinematic viscosity of about 5-50 mm$^2$/s; preferably at least 6, 8 or 10 and at most 40, 35, 30, or 25 mm$^2$/s.
[87] The composition of any one of embodiments 1-85, wherein the coating composition has a kinematic viscosity of about 50-200 mm$^2$/s; preferably at least 60, 70, 80 90 or 100 mm$^2$/s and at most 450, 400, 350, 300 or 250 mm$^2$/s.
[88] The composition of any one of embodiments 1-87, wherein the photo-curable coating composition comprises, based on total dry mass of the composition, 2.0-30 mass % of component (a); 97.8-30 mass % of component (b); 0.2-5 mass % of component (c); and 0-35 mass % of component (d); and wherein the sum of (a)-(d) is 100%.
[89] The composition of any one of embodiments 1-87, wherein the photo-curable coating composition comprises, based on total dry mass of the composition, 3.5-30 mass % of component (a); 96.3-30 mass % of component (b); 0.2-5 mass % of component (c); and 0-35 mass % of component (d); and wherein the sum of (a)-(d) is 100%.
[90] The composition of any one of embodiments 1-87, wherein the photo-curable coating composition comprises, based on total dry mass of the composition, 4-25 mass % of component (a); 95.2-46 mass % of component (b); 0.3-4 mass % of component (c); and 0.5-25 mass % of component (d); and wherein the sum of (a)-(d) is 100%.
[91] The composition of any one of embodiments 1-87, wherein the photo-curable coating composition comprises, based on total dry mass of the composition, 5-20 mass % of component (a); 93.6-46 mass % of component (b); 0.4-3.5 mass % of component (c); and 1-20 mass % of component (d); and wherein the sum of (a)-(d) is 100%.
[92] The composition of any one of embodiments 1-87, wherein the photo-curable coating composition comprises, based on total dry mass of the composition, 2-10 mass % of component (a); 95.5-77 mass % of component (b); 0.5-3 mass % of component (c); and 2-10 mass % of component (d); and wherein the sum of (a)-(d) is 100%.
[93] A method of making the composition of any one of embodiments 1-92, by dissolving all components in a selected solvent under mild conditions.
[94] A hydrophilic coating that has been obtained by drying and curing a layer of the coating composition according to any one of embodiments 1-923.
[95] A lubricious hydrophilic coating that has been obtained by drying and curing a layer of the coating composition according to any one of embodiments 1-92, and by subsequently contacting the dried and cured layer with a wetting agent.
[96] A method of applying a hydrophilic and optionally lubricious coating to an article comprising steps of
Applying a coating composition according to any one of embodiments 1-92 to at least a part of a surface of the article;
At least partly removing the solvent from the applied coating composition;
Photo curing the applied coating composition by exposing to a radiation source during or after removing solvent to form a hydrophilic coating; and
optionally contacting the hydrophilic coating with a wetting agent to form a lubricious coating.
[97] The method of embodiment 96, wherein the coating composition is applied to at least part of a surface by dip-coating, spray coating, wash coating, vapor deposition, brushing or rolling.
[98] The method of any one of embodiments 96-97, wherein the article is a film, a sheet, a rod, a tube, a molded part, a fiber, or a fabric.
[99] The method of any one of embodiments 96-98, wherein the article has a surface that is porous, non-porous, smooth, rough, even or uneven.
[100] The method of any one of embodiments 96-99, wherein the article is elongated and relatively thin, for example a guidewire or catheter, and the coating composition is applied using a dip-coating or a spraying technique.
[101] The method of any one of embodiments 96-100, wherein the coating composition is applied to the surface after cleaning the surface, but without chemically pretreating or applying a primer composition to the surface to be coated.

[102] The method of any one of embodiments 96-101, wherein the radiation source is a UV lamp.

[103] The method of any one of embodiments 96-102, wherein the hydrophilic coating after drying and curing has a thickness from 0.1-300 µm, preferably thickness is at least 0.2, 0.3, 0.4, 0.5 µm, and at most 200, 100, 50, 40, 30, 20 or 15 µm.

[104] The method of any one of embodiments 96-103 or the lubricious hydrophilic coating of embodiment 95, wherein the wetting agent is oil-based or water-based.

[105] The method of any one of embodiments 96-103 or the lubricious hydrophilic coating of embodiment 95, wherein the wetting agent is a water-based or aqueous wetting agent.

[106] The method of any one of embodiments 96-103 or the lubricious hydrophilic coating of embodiment 95, wherein the wetting agent is a water-based composition and further comprises at least one component selected from compounds that lower surface tension and ease spreading of the wetting agent over the coating surface such as surfactants or other organic compounds soluble in water like higher alcohols or glycerol esters; compounds that stabilize the wetted coating like antioxidants such as vitamin E; compounds that enhance retaining water in the wetted hydrophilic coating like salts or urea; compounds that control pH like an organic or inorganic buffer; and antibiotics or antimicrobial compounds.

[107] An article, such as a medical device or a component thereof, having on at least part of its surface a single-layer, hydrophilic, and optionally lubricious coating, which article is obtained by the method of any one of embodiments 96-106.

[108] The article of embodiment 107, wherein the single-layer hydrophilic coating shows after wetting a lubricity of at most 15 g, determined as the averaged friction with the method described in the experimental part using a Harland Friction Tester FTS 6000.

[109] The article of embodiment 108, wherein the single-layer hydrophilic coating shows after wetting a lubricity of at most 14, 13, 12, 11, 10, 9, 8, or 7 g.

[110] The article of any one of embodiments 107-109, which is a substrate for use in the study of living cells and systems, including diagnostic, therapeutic, and experimental human medicine, veterinary medicine, and agricultural fields.

[111] The article of any one of embodiments 107-109, which is a medical device for diagnostic and/or therapeutic application; such as a cardiovascular device, a neurovascular device, a peripheral vascular device, or a device for use in urology, ophthalmology, orthopedics, or general surgery.

[112] The article of embodiment 111, which is a catheter, a guidewire, a delivery device for a valve prosthesis, a delivery device for an intraocular lens, a contact lens, an implantable device, an extracorporeal device, or a medical tool or instrument.

[113] The article of any one of embodiments 111-112, which is an intermittent catheter, a balloon catheter, a PTCA catheter, a stent delivery catheter, a guide wire, a stent, a syringe, a metal or plastic implant, or a medical tubing.

The experiments and samples below further elucidate embodiments of the inventions, but of course, should not be construed as in any way limiting the scope of the claims.

EXPERIMENTS

Compositions
Compounds Used

ComfortCoat® 41002/43003 and 41001/43005 are commercially available, medical grade (primer/topcoat) hydrophilic coating products of DSM Biomedical (Sittard-Geleen, NL).

PEG-DAA, polyethyleneglycol-diacrylamide as prepared from polyethyleneoxide-diamine (Mn 1500 g/mol; Aldrich) and acryloyl chloride as described in WO2008031596A1.

PTGL-TDI-HEA, a copolyether di(urethane acrylate) was prepared from poly(2-methyl-1,4-butanediol)-co-(1,4-butanediol)diol (PTGL, Mn 1000 g/mol; Hodogaya), toluene diisocyanate (TDI; Aldrich) and hydroxy ethylacrylate (HEA; Aldrich) was made as described in WO2008031596A1.

PTGL-IPDI-HEA, a copolyether di(urethane acrylate) was prepared from poly(1,4-butanediol)-co-(2-methyl-1,4-butanediol)diol (PTGL, Mn 1000 g/mol; Hodogaya), isophorone diisocyante (IPDI; Aldrich) and hydroxy ethylacrylate (HEA; Aldrich) was prepared following generalized procedure. An amount of the applicable polyether diol was charged into a 250 ml reactor (equipped with a stirrer, air inlet, dropping funnel, and condenser). After charging, the reactor was heated to 45° C. before the reactor was purged with dry clean air. Then a calculated amount of the applicable diisocyanate (based on 2/1 molar ratio diisocyanate/diol) was charged into the reactor whilst stirring. After this step 1.5 mol % based on diol of BHT was added into the reactor. After waiting one hour for the reaction to start, the temperature was raised to 60° C. and maintained for two additional hours. Then the isocyanate (NCO) content in the mixture was measured using a potentiometric titrator to ensure it was within 10% of the theoretical isocyanate content. If the measured value was not within 10%, the reaction was allowed to continue in additional 15-minute increments and then rechecked until such value was achieved. Then, the calculated amount hydroxyethyl acrylate was added to the mixture, together with 0.1 mol % DBTDL as catalyst. Next the temperature was raised to 85° C. The resulting mixture was reacted for one additional hour at 85° C., after which the NCO content was checked via potentiometric titration. Once the isocyanate content was lower than 0.1% relative to the mass of the components the reaction was stopped; otherwise the mixture was further heated at 85° C. in 15-minute additional increments.

Similarly, as above following polymerizable compounds were prepared:

PTHF-IPDI-HEA, based on poly(tetrahydrofuran)diol (PTHF, Mn 1000 g/mol; Aldrich), isophorone diisocyanate (IPDI; Aldrich) and hydroxy ethyl acrylate (HEA; Aldrich);

PPG1000-IPDI-HEA, based on based on poly(propylene oxide)diol (PPG, Mn 1000 g/mol; Aldrich), IPDI (Aldrich) and (HEA; Aldrich);

PPG2000-TDI-HEA, based on based on poly(propylene oxide)diol (PPG, Mn 2000 g/mol; Aldrich), IPDI (Aldrich) and (HEA; Aldrich);

PPG8000-TDI-HEA, based on based on poly(propylene oxide)diol (PPG, Mn 8000 g/mol; Aldrich), IPDI (Aldrich) and (HEA; Aldrich); and PEG-IPDI-HEA, based on based on poly(ethylene oxide) diol (PPG, Mn 1000 g/mol; Aldrich), IPDI (Aldrich) and (HEA; Aldrich).

As polyvinylpyrrolidon grade PVP K 90, (supplier BASF) was used; unless indicated otherwise.

Benzophenone was obtained from Ciba Specialty Chemicals (tradename Darocure™).

2-hydroxy-1-[4-(hydroxyethoxy)phenyl]-2-methyl-1-propanon (Irgacure™ 2959) was obtained from Aldrich.

Tween 80 (polyoxyethylene (80) sorbitan monooleate) was obtained from Merck.

Ethanol (96%, extra pure) was obtained from Merck.

Coating Compositions

In Tables 1-4 components of coating compositions used in below experiments are listed, except for the solvent ethanol. Indicated mass % thus relates to dry mass of (non-volatiles in) a liquid coating solution, which will substantially correspond to the mass % (of corresponding reacted components) in dried and cured coatings. Compositions were prepared by first dissolving a determined amount of urethane acrylate compounds in ethanol (room temperature, dark), and then adding PVP and other components while gently shaking overnight. The ethanol content of coating compositions varied between about 90 and 98 mass %, depending on targeted solution viscosity. All coating compositions typically had a kinematic viscosity in the range 10-22 mm$^2$/s (as determined using an Ubbelohde viscometer at 25.0±0.3° C.), unless indicated otherwise.

Substrates

The following materials were used as substrate for coating: Polyamide 12 rods of OD 1 mm and length 600 mm (Zeus, item 192124); PVC tubing of 14 Fr (Raumedic AG, DE); polyamide 12 natural tubing of OD 4.7 mm, ID 4.57 mm (Nordson, part #115-2621); Pebax 63D blue, tubing of OD 2.24 mm, ID 2.16 mm (Nordson, part #115-1327); and Pebax 72D, transparent, tubing of OD 1.98 mm, ID 1.22 mm (Nordson, part #115-0678).

Methods

Coating

Polymer rods or tubes of about 40 cm length were dip-coated in a conditioned clean room using an Allmepp CCS-12.175 coater. Intensity of UV lamps was measured with an ILT-1400 meter equipped with an ILT SEL0052224 detector. Polymer rods or tubes (sealed at bottom and with inserted metal wire) were cleaned, each clamped in one of the 12 positions of the coater, immersed with a length of about 30 cm for 10 s in the coating formulation, pulled-up with a speed of 0.5-10 cm/s, and exposed to UV light while being rotated at 4 rpm during 60-360 s. In case of a 2-layer coating system, samples were first dipped in the primer, pulled-up at 1 cm/s and cured during 30 s, and then the topcoat was applied as indicated above. Coated samples were stored in closed PE bags.

Lubricity, Durability and Dry-Out

Tests to determine lubricity and durability of coated samples were performed with a Harland Friction Tester FTS 6000, with the two friction pads applied to the sample with 300 g clamp force and the sample submersed in demi water at room temperature (about 20-22° C.). In case of testing coating on tubing, a wire (or mandrel) was inserted in the tube. 25 test cycles were run, wherein in each cycle the sample was moved upward for 12 cm at 10 mm/s while measuring friction force, the clamp was opened, and sample moved back to starting position. Pads were cleaned after 10, 15 and 20 cycles. Lubricity of the coating is reported as the average friction force of 25 cycles (averaged friction); durability (or wear resistance) of the coating is reported as the difference in average friction force between the last three cycles and the first three cycles (friction change). Reported values are averaged for 10 samples.

An average friction force of 15 g is considered the maximum value for proper lubricity performance; unacceptable damage or even some loss of coating is typically noted in the coating layer if such level is exceeded.

Dry-out behavior of a wetted hydrophilic coating on tubing for a urological catheter, that is the tendency of lubricity to change with time, was also addressed using the Harland friction tester. In this test friction force is measured on a wetted coating layer in air at 20-22° C. and 45-55% relative humidity, at 5 and 10 minutes after wetting. An average friction force of at most 10 g at 10 min. is considered a maximum value for providing a proper lubrication performance of a urinary catheter in actual use by a person.

Shelf Life Evaluation

Shelf life of a coating formulation was assessed by accelerated ageing at 50 and 60° C., and taking samples after 1.5 and 3 months for 60° C. and after 6 months for 50° C. The viscosity, concentrations of photo-initiator and polymerizable compound were determined.

Shelf life of coated product was evaluated by applying the coating formulation on polyamide 12 rods with a pull-up speed of 0.5 cm/s and a cure time of 120 s and initial lubricity and wear performance was evaluated as indicated above. Samples were packaged in pouches and sterilized by exposing to ethylene oxide (about 3 h, 46° C., 0.37 bar EtO; Synergy Health, Venlo NL), and subsequently stored in an oven. Lubricity and wear performance was measured after 6 months storage at 50° C. and after 1.5 and 3 months at 60° C. in an oven to evaluate shelf life of the sterilized coated polyamide 12 rods.

Results

Comparative Experiment a

As reference for Examples 1-19 a commercial two-layer hydrophilic coating system was used, i.e. ComfortCoat® 41002 (primer) and ComfortCoat®43003 (hydrophilic topcoat).

Results in Table 1 indicate that this two layer system can be applied to polyamide 12 (PA 12) substrate rods by dip coating and UV-curing to result in a thin, well-adhering coating, which shows excellent lubricious properties after wetting with water and high durability, that is little change in lubricity during the testing cycles (CE A). In case no primer is used but only the topcoat, no stable and adhering coating could be made on the PA 12 substrate, also not by changing coating conditions.

Examples 1-4 and Comparative Experiments B-D

In these experiments coating compositions were prepared that contain, in addition to ethanol (96%) as solvent, hydrophilic polymer (PVP), two photo-initiators and a surfactant, two distinct polymerizable compounds based on polyetherdiol oligomers with polymerizable endgroups and applied in different mass ratio; that is a polyethylene oxide having acrylamide groups (PEG-DAA) and copolyether of 1,4-butane diol and methylated 1,4-butanediol, with urethane acrylate endgroups (PTGL-TDI-HEA). The results summarized in Table 1 clearly indicate that only if the composition comprises a certain amount of the non-water soluble PTGL-TDI-HEA compound, a crosslinked coating results that combines good adhesion, high lubricity and low wear. In friction testing, a friction force of more than 15 g is seen as indicating the coating having insufficient lubricity. Staining the coating after testing with Congo Red aided in visually determining absence of damage to the coating, which would for example be visible as scratches; and which confirms said friction testing performance.

Examples 5-13

A series of compositions was tested, wherein PTGL-TDI-HEA is applied in different amounts as sole polymerizable polyether, as it appeared that some minimum amount of PTGL-TDI-HEA may be needed for adhesion, whereas a high amount may induce too much cross-linking and reduce lubricity of a coating. Results in Table 1 indicate that an amount of about 4-25 mass % resulted in excellent coating performance, even after only 60 s of UV-curing time. Also presence of a Norrish type I initiator appears not essential, and leaving out the surfactant, which generally improves spreading of the coating on a surface, does not deteriorate friction testing results.

Examples 14-15 and Comparative Experiments E-I

In these experiments several polyether urethane acrylates having different polarities or water-solubilities were evaluated as polymerizable compounds in coating compositions.

Example 14 mainly differs from e.g. Example 6 in that the polymerizable compound was made with an aliphatic diisocyanate instead of an aromatic compound (IPDI vs TDI), and in Example 15 poly(tetrahydrofuran)diol (PTHF) additionally replaced the copolyether. Coating compositions containing these compounds result in hydrophilic coatings showing good performance.

Comparative experiments E-I are performed with polymerizable compounds based on poly(ethylene oxide)diol (PEG) and poly(propylene oxide)diols (PPG). The test results demonstrate that if coating compositions comprise a polyether urethane acrylate as polymerizable compound that is more polar and at least partially soluble in water, insufficient adhesion to PA 12 substrate causes damage and loss of coating during friction testing.

Examples 16-19 and Comparative Experiments J-M

In these experiments performance on coatings made from compositions based on PTGL-IPDI-HEA as polymerizable compound were evaluated on different substrates, which materials are typically used in vascular devices, and compared to the reference two-layer coating system. The results indicate that on all substrates a similar, excellent performance can be obtained.

Shelf Life of Coating Composition and Coated Article

Accelerated ageing experiments were performed using a coating composition according to Example 6 (containing about 97 mass % of ethanol). Ageing at 6 months/50° C. and 3 months/60° C. is considered to translate to a shelf life at ambient conditions of about 4 years.

During testing of the coating composition, concentrations of polymerizable component and initiators, and kinematic viscosity of the solution were determined at the start and after 1.5 and 3 months (60° C.) and 6 months (50° C.). All parameters were found to be stable within experimental error, except for a lowering of about 20% (3 m/60° C.) and 10% (6 m/50° C.) in concentration of the Irganox 2959 initiator component. The aged compositions were subsequently applied to PA 12 substrate and submitted to friction testing, using 300 g and 800 g clamp force. All test results indicated similar coating performance and no deterioration effect of accelerated ageing.

Ageing of a sterilized PA 12 substrate with an applied and cured coating was similarly evaluated with friction testing. Lubricity and durability were found not to be deteriorated by sterilization and ageing at 50 and 60° C.

Comparative Experiment N and Examples 20-24

As reference for other experiments, a commercial two-layer hydrophilic coating system was used; i.e. ComfortCoat® 41001 (primer) and ComfortCoat®43005 (hydrophilic topcoat). This coating system was applied to PVC tubes by dip coating and UV-curing in two steps; to result in a well-adhering coating that shows excellent lubricious properties after wetting with water and good dry-out behavior, e.g. showing little change in lubricity with time. This hydrophilic coating system is typically applied to urinary catheters, with a layer thickness larger than in the previous set of experiments. High lubricity and little dry-out after about 10 minutes are critical performance parameters to persons who routinely need to empty their bladder in a drainage bag using such intermittent catheter system.

It was observed that in case use of the primer was omitted and only the topcoat composition was applied, no stable and adhering coating could be made on the PVC substrate, also not by changing coating conditions.

The experimental results as summarized in Table 4 demonstrate that hydrophilic coating compositions according to present invention and based on ethanol as solvent can also be applied as a single-layer hydrophilic and lubricious coating on a urinary catheter to provide a performance within the desired window (Ex. 20-24), like the commercial reference ComfortCoat® 41001/43005. As the present coating compositions differ considerably from this 2-layer system, e.g. in crosslinker (PTGL-TDI-HEA) and in solvent (ethanol), parameters like crosslinker concentration and viscosity of the coating composition, in combination with coating conditions like pull-up speed and cure time, need optimization. Although test results when applying the composition of Ex. 20 were at the boundary of targeted performance under tested conditions, the data on Ex. 21-24 indicate that by changing processing conditions further improvements are feasible with such composition (see Table 4).

TABLE 1

| | | Coating composition | | | | | Coating conditions | | Friction testing | |
| | | | | | | | | | Lubricity; | Durability; |
| Experiment | Polymerizable compound (mass %) *) | Polyvinyl-pyrrolidone (mass %) *) | Benzo-phenone (mass %) *) | I-2959 (mass %) *) | Tween 80 (mass %) *) | Sub-strate | Pull-up speed (mm/s) | Cure time (s) | averaged friction (g) | friction change (g) |
|---|---|---|---|---|---|---|---|---|---|---|
| CE A [reference] | 2-layer system | ComfortCoat ® 41002/43003 | | | | PA 12 rod | 1 1 | 120 180 | 4.6 ± 0.2 7.2 ± 0.7 | 0.6 ± 0.3 −0.1 ± 0.3 |
| CE B | 8.9 | PEG-DAA | 87.8 | 1.83 | 0.37 | 1.10 | PA 12 rod | 3 | 240 | [>200] | nd |
| CE C | 8.6 3.2 | PEG-DAA PTGL-TDI-HEA | 84.9 | 1.77 | 0.48 | 1.06 | PA 12 rod | 1 | 180 | [>15] | 1.7 ± 3.4 |

TABLE 1-continued

| Experiment | Polymerizable compound (mass %) *) | | Polyvinyl-pyrrolidone (mass %) *) | Benzo-phenone (mass %) *) | I-2959 (mass %) *) | Tween 80 (mass %) *) | Sub-strate | Pull-up speed (mm/s) | Cure time (s) | Lubricity; averaged friction (g) | Durability; friction change (g) |
|---|---|---|---|---|---|---|---|---|---|---|---|
| Ex 1 | 8.3 | PEG-DAA | 82.0 | 1.71 | 0.60 | 1.02 | PA 12 rod | 1 | 180 | 4.3 ± 2.0 | 1.1 ± 3.9 |
|  | 6.4 | PTGL-TDI-HEA | | | | | | | | | |
| Ex 2 | 8.0 | PEG-DAA | 79.1 | 1.65 | 0.71 | 0.99 | PA 12 rod | 5 | 120 | 4.7 ± 0.3 | −0.2 ± 0.3 |
|  | 9.5 | PTGL-TDI-HEA | | | | | | | | | |
| Ex 3 | 7.7 | PEG-DAA | 76.3 | 1.59 | 0.82 | 0.95 | PA 12 rod | 1 | 180 | 3.5 ± 0.4 | −0.2 ± 0.2 |
|  | 12.6 | PTGL-TDI-HEA | | | | | | 3 | 240 | 4.6 ± 0.4 | −0.2 ± 0.2 |
| Ex 4 | 6.6 | PEG-DAA | 65.5 | 1.37 | 1.25 | 0.82 | PA 12 rod | 3 | 240 | 6.4 ± 0.6 | −0.5 ± 0.5 |
|  | 24.4 | PTGL-TDI-HEA | | | | | | | | | |
| CE D | 4.7 | PEG-DAA | 46.1 | 0.96 | 2.02 | 0.58 | PA 12 rod | 3 | 240 | [>15] | 6.6 ± 5 |
|  | 45.7 | PTGL-TDI-HEA | | | | | | | | | |
| Ex 5 | 4.7 | PTGL-TDI-HEA | 91.8 | 1.82 | 0.56 | 1.17 | PA 12 rod | 1 | 120 | 5.2 ± 0.6 | −0.5 ± 0.4 |
|  | | | | | | | | 1 | 180 | 5.2 ± 0.6 | −0.5 ± 0.4 |
| Ex 6 | 7.3 | PTGL-TDI-HEA | 89.5 | 1.41 | 0.62 | 1.15 | PA 12 rod | 1 | 60 | 5.5 ± 0.5 | 0.3 ± 0.6 |
|  | | | | | | | | 1 | 120 | 6.6 ± 0.5 | 1.0 ± 0.6 |
|  | | | | | | | | 1 | 180 | 8.5 ± 0.6 | 0.5 ± 0.4 |
| Ex 7 | 9.0 | PTGL-TDI-HEA | 87.3 | 1.73 | 0.74 | 1.26 | PA 12 rod | 1 | 120 | 4.6 ± 3.2 | −0.5 ± 0.7 |
|  | | | | | | | | 1 | 180 | 5.6 ± 0.2 | −0.8 ± 0.3 |
| Ex 8 | 9.3 | PTGL-TDI-HEA | 88.0 | 0.88 | 0.71 | 1.15 | PA 12 rod | 1 | 120 | 4.9 ± 0.6 | −0.3 ± 0.3 |
| Ex 9 | 9.5 | PTGL-TDI-HEA | 86.1 | 2.55 | 0.54 | 1.35 | PA 12 rod | 1 | 120 | 5.7 ± 0.4 | −0.9 ± 0.4 |
| Ex 10 | 16.7 | PTGL-TDI-HEA | 79.7 | 1.58 | 1.01 | 1.06 | PA 12 rod | 1 | 180 | 6.5 ± 0.2 | −0.9 ± 0.4 |
| Ex 11 | 23.3 | PTGL-TDI-HEA | 73.2 | 1.46 | 1.20 | 0.91 | PA 12 rod | 1 | 180 | 7.6 ± 0.7 | −1.5 ± 0.1 |
| Ex 12 | 7.3 | PTGL-TDI-HEA | 88.9 | 2.67 | 0 | 1.14 | PA 12 rod | 1 | 180 | 5.2 ± 0.7 | −0.8 ± 0.4 |
| Ex 13 | 7.0 | PTGL-TDI-HEA | 89.7 | 2.68 | 0.66 | 0 | PA 12 rod | 1 | 180 | 5.0 ± 0.7 | −0.6 ± 0.5 |

*) mass % based on dry mass of total composition (i.e. excluding solvent)

TABLE 2

| Experiment | Polymerizable compound (mass %) *) | | Polyvinyl-pyrrolidone (mass %) *) | Benzo-phenone (mass %) *) | I-2959 (mass %) *) | Tween 80 (mass %) *) | Sub-strate | Pull-up speed (mm/s) | Cure time (s) | Lubricity; averaged friction (g) | Durability; friction change (g) |
|---|---|---|---|---|---|---|---|---|---|---|---|
| CE A [reference] | 2-layer system | | ComfortCoat ® 41002/43003 | | | | PA 12 rod | 1 | 120 | 4.6 ± 0.2 | 0.6 ± 0.3 |
|  | | | | | | | | 1 | 180 | 7.2 ± 0.7 | −0.1 ± 0.3 |
| Ex 14 | 6.8 | PTGL-IPDI-HEA | 89.8 | 1.32 | 0.64 | 1.36 | PA 12 rod | 1 | 60 | 8.7 ± 7.6 | 4.5 ± 7.9 |
|  | | | | | | | | 1 | 120 | 5.4 ± 0.3 | 1.1 ± 0.8 |
|  | | | | | | | | 1 | 180 | 9.6 ± 2.5 | 2.8 ± 4.1 |
| Ex 15 | 7.0 | PTHF-IPDI-HEA | 89.7 | 1.42 | 0.65 | 1.20 | PA 12 rod | 1 | 60 | 6.9 ± 1.2 | 1.1 ± 1.1 |
|  | | | | | | | | 1 | 120 | 5.7 ± 0.5 | 0.8 ± 0.6 |
|  | | | | | | | | 1 | 180 | 7.9 ± 0.9 | 1.8 ± 0.6 |
| CE E | 7.2 | PPG1000-IPDI-HEA | 89.5 | 1.44 | 0.66 | 1.20 | PA 12 rod | 1 | 120 | [>15] | |
| CE F | 7.0 | PPG2000-TDI-HEA | 89.8 | 1.38 | 0.64 | 1.16 | PA 12 rod | 1 | 120 | [>15] | |
| CE G | 12.8 | PPG2000-TDI-HEA | 84.2 | 1.29 | 0.64 | 1.06 | PA 12 rod | 1 | 120 | [>15] | |
| CE H | 7.0 | PPG8000-TDI-HEA | 89.7 | 1.36 | 0.58 | 1.34 | PA 12 rod | 1 | 120 | [>15] | |
| CE I | 7.0 | PEG-IPDI-HEA | 89.6 | 1.38 | 0.62 | 1.44 | PA 12 rod | 1 | 120 | [>15] | |

*) mass % based on dry mass of total composition (i.e. excluding solvent)

TABLE s

| Experiment | Coating composition Polymerizable compound (mass %) *) | Polyvinyl-pyrrolidone (mass %) *) | Benzo-phenone (mass %) *) | I-2959 (mass %) *) | Tween 80 (mass %) *) | Coating conditions Substrate | Pull-up speed (mm/s) | Cure time (s) | Friction testing Lubricity; averaged friction (g) | Durability; friction change (g) |
|---|---|---|---|---|---|---|---|---|---|---|
| CE J [reference] | 2-layer system | | ComfortCoat ® 41002/43003 | | | PVC tube | 1 | 180 | 7.5 ± 0.7 | −0.1 ± 0.3 |
| Ex 16 | 7.7 PEG-DAA 12.6 PTGL-IPDI-HEA | 76.3 | 1.59 | 0.82 | 0.95 | PVC tube | 1 2 | 180 240 | 12.0 ± 1.6 7.8 ± 10.7 | 0.8 ± 0.7 −1.6 ± 0.5 |
| CE K [reference] | 2-layer system | | ComfortCoat ® 41002/43003 | | | PA 12 tube | 0.5 | 120 | 10.1 ± 1.0 | −0.3 ± 0.3 |
| Ex 17 | 9.2 PTGL-IPDI-HEA | 87.2 | 1.75 | 0.72 | 1.09 | PA 12 tube | 0.5 | 120 | 114 ± 28 | −0.8 ± 0.4 |
| CE L [reference] | 2-layer system | | ComfortCoat ® 41002/43003 | | | Pebax 63D rod | 0.5 | 120 | 2.9 ± 0.5 | 0.2 ± 0.2 |
| Ex 18 | 9.2 PTGL-IPDI-HEA | 87.2 | 1.75 | 0.72 | 1.09 | Pebax 63D rod | 0.5 | 120 | 2.5 ± 0.2 | 0.2 ± 0.2 |
| CE M [reference] | 2-layer system | | ComfortCoat ® 41002/43003 | | | Pebax 72D rod | 0.5 | 120 | 3.6 ± 0.5 | 0.2 ± 0.6 |
| Ex 19 | 9.2 PTGL-IPDI-HEA | 87.2 | 1.75 | 0.72 | 1.09 | Pebax 72D rod | 0.5 | 120 | 3.1 ± 0.2 | −0.1 ± 0.2 |

*) mass % based on dry mass of total composition (i.e. excluding solvent)

TABLE 4

| Experiment | Coating composition Polymerizable compound (mass %) *) | PVP | Benzo-phenone | I-2959 (mass %) *) | Tween 80 | Viscosity (mm²/s) | Coating conditions Substrate | Pull-up speed (mm/s) | Cure time (s) | Friction testing Lubricity- averaged friction (g) | Durability- friction change (g) | Dry-out; friction at 10 min. (g) |
|---|---|---|---|---|---|---|---|---|---|---|---|---|
| CE N [reference] | 2-layer system | ComfortCoat ® 41001/43005 | | | | 90 (topcoat) | PVC tube | 10 | 360 | 2.9 ± 0.3 | −0.8 ± 0.4 | 3.8 ± 0.6 |
| Ex 20 | 7.0 PTGL-TDI-HEA | 89.6 | 1.7 | 0.6 | 1.1 | 120 | PVC tube | 10 | 120 | 14.7 ± 2.7 | −2.3 ± 1.3 | — [30% > 10] ??? |
| Ex 21 | 4.5 PTGL-TDI-HEA | 92.3 | 2.0 | 0.5 | 0.7 | 70 | PVC tube | 10 | 120 | 5.6 ± 0.6 | −1.1 ± 0.5 | 6.4 ± 1.2 |
| Ex 22 | 4.5 PTGL-TDI-HEA | 92.3 | 2.0 | 0.5 | 0.7 | 70 | PVC tube | 10 | 150 | 7.7 ± 0.8 | −0.7 ± 0.4 | 6.8 ± 1.8 |
| Ex 23 | 2.3 PTGL-TDI-HEA | 94.0 | 2.1 | 0.5 | 1.1 | 78 | PVC tube | 10 | 120 | 7.6 ± 0.4 | −2.3 ± 0.5 | 5.8 ± 2.2 |
| Ex 24 | 2.3 PTGL-TDI-HEA | 94.0 | 2.1 | 0.5 | 1.1 | 78 | PVC tube | 10 | 180 | 7.9 ± 1.1 | −2.0 ± 1.0 | 7.9 ± 1.8 |

*) mass % based on dry mass of total composition (i.e. excluding solvent)

The invention claimed is:

1. A photo-curable hydrophilic coating composition comprising:
(a) a polymerizable compound of formula [1], wherein G is a residue of a hydrophobic hydroxy-functional oligomer; n is 1-10, each $R_1$ independently is a residue of a $C_6$-$C_{20}$ aliphatic, cycloaliphatic, or aromatic hydrocarbon compound, and Z is a moiety having an unsaturated polymerizable group;
(b) a hydrophilic polymer;
(c) a photo-initiator;
(d) optionally one or more further components; and
(e) a solvent for components (a)-(c); wherein
the polymerizable compound of formula [1] is present in an amount of 2.0-30 mass % based on the total dry mass of the composition, and wherein
$R_1$ is a residue of 2,4-toluene, 2,6-toluene, hexane, butane, cyclohexane or isophorone.

2. The coating composition according to claim 1, wherein n is 1.8-3.

3. The coating composition according to claim 1, wherein G is a residue of a hydroxy-functional hydrophobic oligomer chosen from the group consisting of polyethers, polyesters, polycarbonates, polyurethanes, polyepoxides, polyamides, poly(meth)acrylamides, poly(meth)acrylates, and polyolefins, or any combination thereof.

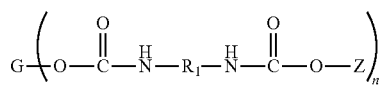

[1]

4. The coating composition according to claim 1, wherein the hydroxy-functional oligomer is a polyether.

5. The coating composition according to claim 1, wherein Z is a (meth)acrylic moiety of formula [2]:

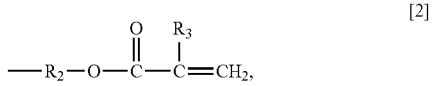
[2]

wherein
each $R_2$ independently is a $C_1$-$C_{10}$ alkyl, and each $R_3$ independently is hydrogen or methyl.

6. The coating composition according to claim 1, wherein the polymerizable compound of formula [1] is the reaction product of a polyether diol based on tetrahydrofuran or comprising tetrahydrofuran and methyl tetrahydrofuran, toluene diisocyanate, and hydroxyethyl acrylate.

7. The coating composition according to claim 1, wherein the hydrophilic polymer comprises a non-ionic polymer.

8. The coating composition according to claim 1, wherein the photo-initiator comprises a Norrish type II initiator.

9. The coating composition according to claim 1, further comprising a surfactant, an antioxidant, an osmolality-increasing compound, and/or a hydrophilic polymerizable compound.

10. The coating composition according to claim 1, wherein the composition contains 40-99.5 mass % of solvent, which solvent is a polar organic liquid miscible with water.

11. The coating composition according to claim 1 comprising, based on total dry mass of the composition,
2.0-30 mass % of the component (a);
97.8-30 mass % of the component (b);
0.2-5 mass % of the component (c); and
0-35 mass % of the component (d); and wherein
the sum of the components (a)-(d) is 100%.

12. A method of applying a hydrophilic and optionally lubricious coating to an article comprising steps of:
   (i) applying a coating composition according to claim 1 to at least a part of a surface of the article;
   (ii) at least partly removing the solvent from the applied coating composition;
   (iii) curing the applied coating composition by exposing to a radiation source during or after removing solvent to form a hydrophilic coating; and
   (iv) optionally contacting the hydrophilic coating with a wetting agent to form a lubricious coating.

13. A medical device or a component thereof, having on at least part of its surface a single-layer, hydrophilic, and optionally lubricious coating, which article is obtained by the method of claim 12.

14. The coating composition according to claim 1, wherein n is 1.8-2.2.

15. The coating composition according to claim 1, wherein the hydroxy-functional oligomer is a polytetrahydrofuran diol or a poly(tetrahydrofuran-co-methyl tetrahydrofuran) diol.

16. The coating composition according to claim 1, wherein the polymerizable group is a (meth)acrylic group.

17. The coating composition according to claim 15, wherein R1 is a residue of 2,4-toluene, 2,6-toluene, hexane, butane, cyclohexane, or isophorone.

18. The coating composition according to claim 17, wherein n is 1.8-2.2 and the polymerizable group is a (meth)acrylic group.

* * * * *